United States Patent
Carmeliet et al.

(10) Patent No.: US 10,106,601 B2
(45) Date of Patent: Oct. 23, 2018

(54) INHIBITION OF PLGF TO TREAT PHILADELPHIA CHROMOSOME POSITIVE LEUKEMIA

(75) Inventors: Peter Carmeliet, Blanden (BE); Sonja Loges, Heverlee (BE)

(73) Assignees: VIB VZW, Ghent (BE); Life Sciences Research Partners VZW, Leuven (BE)

( * ) Notice: Subject to any disclaimer, the term of this patent is extended or adjusted under 35 U.S.C. 154(b) by 220 days.

(21) Appl. No.: 13/122,137

(22) PCT Filed: Oct. 2, 2009

(86) PCT No.: PCT/EP2009/062861
§ 371 (c)(1),
(2), (4) Date: Jun. 28, 2011

(87) PCT Pub. No.: WO2010/037864
PCT Pub. Date: Apr. 8, 2010

(65) Prior Publication Data
US 2011/0250209 A1    Oct. 13, 2011

Related U.S. Application Data

(60) Provisional application No. 61/195,140, filed on Oct. 2, 2008.

(51) Int. Cl.
| | | |
|---|---|---|
| *A61K 39/395* | (2006.01) | |
| *A61K 39/00* | (2006.01) | |
| *C07K 16/00* | (2006.01) | |
| *C07K 16/22* | (2006.01) | |
| *C07K 16/28* | (2006.01) | |

(52) U.S. Cl.
CPC .......... *C07K 16/22* (2013.01); *C07K 16/2863* (2013.01); *A61K 2039/505* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,545,806 A | 8/1996 | Lonberg et al. | |
| 5,851,999 A | 12/1998 | Ullrich et al. | |
| 5,919,899 A | 7/1999 | Persico et al. | |
| 6,365,157 B2 | 4/2002 | Rockwell et al. | |
| 6,369,204 B1 | 4/2002 | Kim et al. | |
| 7,482,004 B2 * | 1/2009 | Carmeliet | A61K 38/07 424/145.1 |
| 7,642,239 B2 * | 1/2010 | Taylor et al. | 514/1.1 |
| 2003/0180286 A1 * | 9/2003 | Carmeliet et al. | 424/130.1 |

FOREIGN PATENT DOCUMENTS

| | | |
|---|---|---|
| JP | 2001/086982 | 4/2001 |
| WO | WO 84/03564 | 9/1984 |
| WO | WO 96/30046 | 10/1996 |
| WO | WO 97/15330 | 5/1997 |
| WO | WO 98/13071 | 4/1998 |
| WO | WO 99/24056 | 5/1999 |
| WO | WO 99/60846 | 12/1999 |
| WO | WO 01/85796 | 11/2001 |
| WO | WO 03/000183 | 1/2003 |
| WO | WO 03/103581 | 12/2003 |
| WO | WO 2006/099698 A2 | 9/2006 |
| WO | WO 2007/047609 | 4/2007 |
| WO | WO 2007/047609 A2 | 4/2007 |

OTHER PUBLICATIONS

Cortes, Jorge E, et al. Investigational strategies in chronic myelogenous leukemia. (2004) Hematology/Oncology Clinics of North America, 18 93), pp. 619-639.*
Cortes et al. Investigational strategies in chronic myelogenous leukemia. Hematology/Oncology Clinics of North America. 18:619-639, 2004.*
Ikai et al. Placenta growth factor stimulates the growth of Philadelphia chromosome positive acute lymphoblastic leukemia cells by both autocrine and paracrine pathways European Journal of Haematology. 2005; 75: 273-279.*
Fragoso et al. VEGFR-1 (FLT-1) activation modulates acute lymphoblastic leukemia localization and survival within the bone marrow, determining the onset of extramedullary disease. Blood. 2006; 107: 1608-1616.*
Van de Veire et al. Evidence for the efficacy of PIGF inhibition in age-related macular degeneration. Acta Ophthalmoligica, 2010; 88(Suppl. S246).*
Bais et al. PlGF Blockade Does Not Inhibit Angiogenesis during Primary Tumor Growth. Cell, 2010; 141:166-177.*
Vajdos et al. Comprehensive functional maps of the antigen-binding site of an anti-ErbB2 antibody obtained with shotgun scanning mutagenesis. Journal of Molecular Biology, Jul. 5, 2002;320(2):415-28.*
Brown et al. Tolerance to single, but not multiple, amino acid replacements in antibody VH CDR2. Journal of Immunology, May 1996;156(9):3285-91.*
Fundamental Immunology 242 (William E. Paul, M.D. ed., 3d ed. 1993 (Year: 1993).*
Ikai, et al. "Placenta Growth Factor Stimulates the Growth of Philadelphia Chromosome Positive Acute Lymphoblastic Leukemia Cells by Both Autocrine and Paracrine Pathways," *European Journal of Haematology*, vol. 75, No. 4, pp. 273-279, Oct. 2005.
Fragoso, et al. "VEGFR-1 (FLT-1) Activation Modulates Acute Lymphoblastic Leukemia Localization and Survival within the Bone Marrow, Determining the Onset of Extramedullary Disease," *Blood*, vol. 107, No. 4, pp. 1608-1616, Feb. 2006.

(Continued)

*Primary Examiner* — Vanessa L. Ford
*Assistant Examiner* — Sandra E Dillahunt
(74) *Attorney, Agent, or Firm* — Knobbe, Martens, Olson & Bear, LLP

(57) ABSTRACT

The present application relates to the field of leukemias, and more in particular to how P1 GF inhibition can help to treat Philadelphia chromosome positive (Ph+) leukemias. Methods are provided for treating Ph+ leukemias by administering P1 GF inhibitors. Also disclosed are uses of P1 GF inhibitors in the treatment of Ph+ leukemias, or for the preparation of a medicament against Ph+ leukemias.

11 Claims, 9 Drawing Sheets

Specification includes a Sequence Listing.

(56) References Cited

OTHER PUBLICATIONS

Cortes, et al. "Investigational Strategies in Chronic Myelogenous Leukemia," *Hematology/Oncology Clinics of North America*, vol. 18, No. 3, pp. 619-639, Jun. 1, 2004.
Shirasaki, et al. "Vascular Endothelial Growth Factor Plays an Important Role in Chronic Myelogenous Leukemia: Relationship to Disease-Progression," *Haematologica*, vol. 93, Supplement 1, pp. 538-539, Jun. 1, 2008.
Verstovsek, et al. "Clinical Relevance of VEGF Receptors 1 and 2 in Patients with Chronic Myelogenous Leukemia," *Leukemia Research*, vol. 27, No. 7, pp. 661-669, Jul. 2003.
Verstovsek, et al. "Prognostic Significance of Cellular Vascular Endothelial Growth Factor Expression in Chronic Phase Chronic Myeloid Leukemia," *Blood*, vol. 99, No. 6, pp. 2265-2267, Mar. 15, 2002.
Fischer, et al. "Anti-PlGF Inhibits Growth of VEGF(R)-Inhibitor-Resistant Tumors without Affecting Healthy Vessels," *Cell*, vol. 131, No. 3, pp. 463-475, Nov. 2, 2007.
Luttun, et al. "Genetic Dissection of Tumor Angiogenesis: are PlGF and VEGFR-1 Novel Anti-cancer Targets?," *Biochimica et Biophysica Acta*, vol. 1654, No. 1, pp. 79-94, Mar. 4, 2004.
May, et al. "Peptide Epitopes from the Wilms' Tumor 1 Oncoprotein Stimulate CD4+ and CD8+ T Cells that Recognize and Kill Human Malignant Mesothelioma Tumor Cells," *Clinical Cancer Research*, vol. 13, No. 15, Pt. 1, pp. 4547-4555, Aug. 1, 2007.
Puccetti, et al. "BCR-ABL Mediates Arsenic Trioxide-induced Apoptosis Independently of Its Aberrant Kinase Activity," *Cancer Research*, vol. 60, No. 13, pp. 3409-3413, Jul. 1, 2000.
Loges, et al. "Evaluation of the Role of PlGF and the Therapeutic Potential of Anti-PlGF in BCR/ABL+ Leukemia," *Blood*, vol. 112, No. 11, pp. 399-400, Nov. 2008.
International Search Report dated May 17, 2010, issued to international patent application No. PCT/EP2009/062861.
Notice of Opposition Strawman Limited in European Patent EP 1297016B1 filed Aug. 6, 2009, dated Dec. 20, 2006.
Interlocutory Decision of Opposition Division in Opposition of Opponent Strawman Limited in European Patent EP 1297016B1 filed Aug. 6, 2009, dated Mar. 27, 2009.
Statement of Grounds of Appeal of Opponent Strawman Limited in European Patent EP 1297016 B1 filed Aug. 6, 2009, dated Aug. 6, 2009.
Ahmed et al., "Regulation of Placental Vascular Endothelial Growth Factor (VEGF) and Placenta Growth Factor (PlGF) and Soluble Flt-1 by Oxygen—A Review," *Placenta*, vol. 21, Supplement A, Trophoblast Research, 14, pp. S16-S24 (2000).
Bais et al., "PlGF Blockade Does Not Inhibit Angiogenesis during Primary Tumor Growth," *Cell*, vol. 141, pp. 166-177 (Apr. 2, 2010).
Barillari et al., "The Basic Residues of Placenta Growth Factor Type 2 Retrieve Sequestered Angiogenic Factors into a Soluble Form," *Am J Pathol*, vol. 152(5), pp. 1161-1166 (May 1998).
Bernatchez et al., "Vascular Endothelial Growth Factor Effect on Endothelial Cell Proliferation, Migration, and Platelet-activating Factor Synthesis Is Flk-1-dependent," *The Journal of Biological Chemistry*, vol. 274(43), Issue of Oct. 22, pp. 31047-31054 (1999).
Bicknell et al., *Tumor Angiogenesis*, chapter 2, pp. 1-3 and 5-18 (1997).
Bottomley et al., "Placenta growth factor (PlGF) induces vascular endothelial growth factor (VEGF) secretion from mononuclear cells and is co-expressed with VEGF in synovial fluid," *Clin Exp Immunol*, vol. 119, pp. 182-188 (2000).
Boulton et al., "Placental growth factor localisation in diabetic retinas and preretinal membranes," *Investigative Ophthalmology & Visual Science*, vol. 38(4), p. S965 (Mar. 15, 1997).
Brenchley et al., "Angiogenesis in inflammatory joint disease: a target for therapeutic intervention," *Clin Exp Immunol*, vol. 121, pp. 426-429 (2000).
Carmeliet, "Basic Concepts of (Myocardial) Angiogenesis: Role of Vascular Endothelial Growth Factor and Angiopoietin," *Current Interventional Cardiology Reports*, vol. 1, pp. 322-335 (1999).
Carmeliet, "Gene targeting and gene transfer to unravel the molecular basis of the formation and disorders of blood vessels," *Verhandelingen—Koninklijke Academie voor Geneeskunde*, vol. 62(1), pp. 31-68 (2000).
Carmeliet, "Molecular mechanisms of normal and pathologic angiogenesis: Insights and therapeutic concepts from transgenic mice," *J Vascular Res*, vol. 37, Suppl. 1, p. 79 (Abstract) (2000).
Carmeliet et al., "Molecular analysis of blood vessel formation and disease," *Am J Physiol Heart Circ Physiol*, vol. 273, pp. H2091-H2104 (1997).
Carmeliet et al., "Role of Vascular Endothelial Growth Factor and Vascular Endothelial Growth Factor Receptors in Vascular Development," *Curr Top Microbial Immunol*, vol. 237, pp. 133-158 (1999).
Carmeliet et al., "Transgenic mouse models in angiogenesis and cardiovascular disease," *J Pathol*, vol. 190, pp. 387-405 (2000).
Carmeliet et al., "Mechanisms of angiogenesis and arteriogenesis," *Nature Medicine*, vol. 6(3), pp. 389-395 (Mar. 2000).
Carmeliet et al., "Synergism between vascular endothelial growth factor and placental growth factor contributes to angiogenesis and plasma extravasation in pathological conditions," *Nature Medicine*, vol. 7(5), pp. 575-593 (May 2001).
Chen et al., "Selection and Analysis of an Optimized Anti-VEGF Antibody: Crystal Structure of an Affinity-matured Fab in Complex with Antigen," *J Mol Biol*, vol. 293, pp. 865-881 (1999).
Christinger et al., "The Crystal Structure of Placental Growth Factor in Complex with Domain 2 of Vascular Endothelial Growth Factor Receptor-1," *J Biol Chem*, vol. 279(11), Issue of Mar. 12, pp. 10382-10388 (2004).
Colucciello, "Diabetic retinopathy, Control of systemic factors preserves vision," *Postgraduate Medicine* online, vol. 116(1), (Jul. 2004).
Declerck et al., "Generation of Monoclonal Antibodies against Autologous Proteins in Gene-inactivated Mice," *J Biol Chem*, vol. 270(15), Issue of Apr. 14, pp. 8397-8400 (1995).
Dias et al., "Inhibition of both paracrine and autocrine VEGF/VEGFR-2 signaling pathways is essential to induce long-term remission of xenotransplanted human leukemias," *PNAS*, vol. 98(19), pp. 10857-10862 (Sep. 11, 2001).
Donnini et al., "Expression and localization of placenta growth factor and PlGF receptors in human meningiomas," *J Pathology*, vol. 189, pp. 66-71 (1999).
Fischer et al., "Anti-PlGF Inhibits Growth of VEGF(R)-Inhibitor-Resistant Tumors without Affecting Healthy Vessels," *Cell*, vol. 131, Supplementary Data, pp. 463-475 (2007).
Folkman, "Clinical applications of research on angiogenesis," *N Engl J Med*, vol. 333(26), pp. 1757-1763 (Dec. 28, 1995).
Griffioen et al., "Angiogenesis: Potentials for Pharmacologic Intervention in the Treatment of Cancer, Cardiovascular Diseases, and Chronic Inflammation," *Pharmacology Rev*, vol. 52(2), pp. 237-268 (2000).
Guidi et al., "Expression of Vascular Permeability Factor (Vascular Endothelial Growth Factor) and Its Receptors in Endometrial Carcinoma," *Cancer*, vol. 78(3), pp. 454-460 (Aug. 1, 1996).
Gura, "Systems for Identifying New Drugs Are Often Faulty," *Science*, vol. 278, pp. 1041-1042 (Nov. 7, 1997).
Hansma et al., "Recombinant human endostatin administered as a 28-day continuous intravenous infusion, followed by daily subcutaneous injections: a phase I and pharmacokinetic study in patients with advanced cancer," *Annals of Oncology*, vol. 16, pp. 1695-1701 (2005).
Hazelton et al., "Vascular Endothelial Growth Factor in Ovarian Cancer," *Curr Oncol Rep*, vol. 1, pp. 59-63 (1999).
Holm et al., "Functional mapping and single chain construction of the anti-cytokeratin 8 monoclonal antibody TS1," *Mol Immunol*, vol. 44, pp. 1075-1084 (2007).
Inoue et al., "Mechanism of mustard oil-induced skin inflammation in mice," *Eur J Pharmacol*, vol. 333, pp. 231-240 (1997).
Iyer et al., "The Crystal Structure of Human Placenta Growth Factor-1 (PlGF-1), an Angiogenic Protein, at 2.0 Å Resolution," *J Biol Chem*, vol. 276, 15, pp. 12153-12161 (2001).
Jain et al., "PlGF: A New Kid on the Antiangiogenesis Block," *Cell*, vol. 131, pp. 443-445 (Nov. 2, 2007).

(56) References Cited

OTHER PUBLICATIONS

Johnstone et al., *Immunochemistry in Practice*, Blackwell Scientific Publications, Oxford; p. 30 (1987).

Kanno et al., "Roles of two VEGF receptors, Flt-1 and KDR, in the signal transduction of VEGF effects in human vascular endothelial cells," *Oncogene*, vol. 19, pp. 2138-2146 (2000).

Katoh et al., "Expression of Vascular Endothelial Growth Factor (VEGF) in Human Thyroid Neoplasms," *Human Pathol*, vol. 30(8), pp. 891-897 (Aug. 1999).

Khaliq et al., "Increased Expression of Placenta Growth Factor in Proliferative Diabetic Retinopathy," *Laboratory Investigation*, vol. 78(1), p. 109 (1998).

Köhler et al., "Continuous cultures of fused cells secreting antibody of predefined specificity," *Nature*, vol. 256, pp. 495-497 (Aug. 7, 1975); reprinted in *J Immunol*, vol. 174, pp. 2453-2455 (2005).

Laurin et al., "Paget Disease of Bone: Mapping of Two Loci at 5q35-qter and 5q31," *Am J Hum Genet*, vol. 69, pp. 528-543 (2001).

Lou, "PIGF point—counterpoint," *SciBX*, vol. 3(16), pp. 5-7 (Apr. 22, 2010).

Luttun et al., "Loss of placental growth factor protects mice against vascular permeability in pathological conditions," *Biochem Biophys Res Comm*, vol. 295, pp. 428-434 (2002).

Maccallum et al., "Antibody-antigen Interactions: Contact Analysis and Binding Site Topography," *J Mol Biol*, vol. 262, pp. 732-745 (1996).

Maglione et al., "Isolation of a human placenta cDNA coding for a protein related to the vascular permeability factor," *PNAS*, vol. 88, pp. 9267-9271 (1991).

Maglione et al., "Two alternative mRNAs coding for the angiogenic factor, placenta growth factor (PlGF), are transcribed from a single gene of chromosome 14," *Oncogene*, vol. 8, pp. 925-931 (1993).

Maragoudakis, "Proceedings of the 5$^{th}$ Biannual International Meeting on Angiogenesis: From the Molecular to Integrative Pharmacology, held Jul. 1-7, 1999, in Crete, Greece," *Advances in Experimental Medicine and Biology*, vol. 476, pp. 1-4 (2000).

Mayr-Wohlfart et al., "Vascular Endothelial Growth Factor Stimulates Chemotactic Migration of Primary Human Osteoblasts," *Bone*, vol. 30(3), pp. 472-477 (Mar. 2002).

Migdal et al., "Neuropilin-1 Is a Placenta Growth Factor-2 Receptor," *The Journal of Biological Chemistry*, vol. 273(35), Issue of Aug. 28, pp. 22272-22278 (1998).

Miller, "Issues and challenges for antiangiogenic therapies," *Breast Cancer Research and Treatment*, vol. 75, pp. S45-S50 (2002).

Mitamura et al., "Placenta growth factor and vascular endothelial growth factor in the vitreous of patients with proliferative vitreoretinopathy," *Clinical and Experimental Ophthalmology*, vol. 33, pp. 226-228 (2005).

MSNBC News Services, online news, "Mixed results on new cancer drugs" (Nov. 9, 2000).

Mueller et al., "Expression of tissue factor by melanoma cells promotes efficient hematogenous metastasis," *PNAS*, vol. 89, pp. 11832-11836 (Dec. 1992).

Nicol et al., "Vascular endothelial growth factor expression is increased in renal cell carcinoma," *J Urol*, vol. 157, pp. 1482-1486 (Apr. 1997).

Niida et al., "Vascular Endothelial Growth Factor Can Substitute for Macrophage Colony-stimulating Factor in the Support of Osteoclastic Bone Resorption," *J Exp Med*, vol. 190(2), pp. 293-298 (Jul. 19, 1999).

Nomura et al., "Placenta growth factor (PIGF) mRNA expression in brain tumors," *J Neuro-Oncol*, vol. 40, pp. 123-130 (1998).

Oliver et al., "Suppression of Collagen-Induced Arthritis by an Angiogenesis Inhibitor, AGM-1470, in Combination with Cyclosporin: Reduction of Vascular Endothelial Growth Factor (VEGF)," *Cell Immunol*, vol. 166, pp. 196-206 (1995).

Paleolog et al., "Angiogenesis in arthritis: role in disease pathogenesis and as a potential therapeutic target," *Angiogenesis*, vol. 2, pp. 295-307 (1998/1999).

Paques et al., "Growth factors and diabetic retinopathy," *Diabetes & Metabolism (Paris)*, vol. 23, pp. 125-130 (1997).

Park et al., "Placenta Growth Factor, Potentiation of vascular endothelial growth factor bioactivity, in vitro and in vivo, and high affinity binding to Flt-1 but not to Flk-1/KDR," *JBC*, vol. 269(41), Issue of Oct. 14, pp. 25646-25654 (1994).

Parry et al., "Bioactivity of anti-angiogenic ribozymes targeting *Flt-1* and *KDR* mRNA," *Nucleic Acids Research*, vol. 27(13), pp. 2569-2577 (1999).

Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J Immunol*, vol. 169, pp. 3076-3084 (2002).

Queen et al., "A humanized antibody that binds to the interleukin 2 receptor," *PNAS*, vol. 86, pp. 10029-10033 (Dec. 1989).

R&D Systems, "Monoclonal Anti-mouse PIGF•2 Antibody," datasheet (Oct. 18, 1999).

R&D Systems, "Biotinylated Anti-mouse PIGF-2 Antibody" datasheet (Jan. 21, 1999).

R&D Systems, "Monoclonal Anti-human PIGF•Antibody," datasheet (Jun. 26, 2001).

Robinson et al., "Nonvascular role for VEGF: VEGFR-1, 2 activity is critical for neural retinal development," *The FASEB Journal*, vol. 15, pp. 1215-1217 (May 2001).

Rudikoff et al., "Single amino acid substitution altering antigen-binding specificity," *PNAS*, vol. 79, pp. 1979-1983 (Mar. 1982).

Ryan et al., "Preclinical Safety Evaluation of rhuMAbVEGF, an Antiangiogenic Humanized Monoclonal Antibody," *Toxicologic Pathology*, vol. 27(1), pp. 78-86 (1999).

Skolnick et al., "From genes to protein structure and function: novel applications of computational approaches in the genomic era," *Trends Biotech*, vol. 18, pp. 34-39 (Jan. 2000).

Takahashi et al., "Markedly Increased Amounts of Messenger RNAs for Vascular Endothelial Growth Factor and Placenta Growth Factor in Renal Cell Carcinoma Associated with Angiogenesis," *Cancer Research*, vol. 54, pp. 4233-4237 (Aug. 1, 1994).

Vajdos et al., "Comprehensive Functional Maps of the Antigenbinding Site of an Anti-ErbB2 Antibody Obtained with Shotgun Scanning Mutagenesis," *J Mol Biol*, vol. 320, pp. 415-428 (2002).

Van De Veire et al., "Further Pharmacological and Genetic Evidence for the Efficacy of PlGF Inhibition in Cancer and Eye Disease," *Cell*, vol. 141, pp. 178-190 (Apr. 2, 2010).

Viglietto et al., "Upregulation of vascular endothelial growth factor (VEGF) and downregulation of placenta growth factor (PIGF) associated with malignancy in human thyroid tumors and cell lines," *Oncogene*, vol. 11, pp. 1569-1579 (1995).

Viglietto et al., "Neovascularization in human germ cell tumors correlates with a marked increase in the expression of the vascular endothelial growth factor but not the placenta-derived growth factor," *Oncogene*, vol. 13, pp. 577-587 (1996).

Weindel et al., "Detection and Quantification of Vascular Endothelial Growth Factor/Vascular Permeability Factor in Brain Tumor Tissue and Cyst Fluid: The Key to Angiogenesis?" *Neurosurgery*, vol. 35(3), pp. 439-449 (Sep. 1994).

Wu et al., "Humanization of a Murine Monoclonal Antibody by Simultaneous Optimization of Framework and CDR Residues," *J Mol Biol*, vol. 294, pp. 151-162 (1999).

Yonekura et al., "Placenta Growth Factor and Vascular Endothelial Growth Factor B and C Expression in Microvascular Endothelial Cells and Pericytes, implication in autocrine and paracrine regulation of angiogenesis," *JBC*, vol. 274(49), Issue of Dec. 3, pp. 35172-35178 (1999).

Ziche et al., "Placenta Growth Factor-1 is Chemotactic, Mitogenic, and Angiogenic," *Laboratory Investigation*, vol. 76(4), pp. 517-531 (1997).

Ratajczak et al., "Role of vascular endothelial growth factor (VEGF) and placenta-derived growth factor (PIGF) in regulating human haemopoietic cell growth," *British Journal of Haematology*, vol. 103, pp. 969-979 (1998).

Shah et al., "Multiple *BCR-ABL* kinase domain mutations confer polyclonal resistance to the tyrosine kinase inhibitor imatinib (STI571) in chronic phase and blast crisis chronic myeloid leukemia," *Cancer Cell*, vol. 2, pp. 117-125 (Aug. 2002).

(56) References Cited

OTHER PUBLICATIONS

Wang, Yinxing, et al., National Cancer Diagnosis and Treatment Science Research Symposium, pp. 28-40 (Jun. 1, 2005).
Weisberg et al., "Mechanism of resistance to the ABL tyrosine kinase inhibitor STI571 in BCR/ABL—transformed hematopoietic cell lines," *Blood*, vol. 95(11), pp. 3498-3505 (Jun. 1, 2000).
Druker et al., "Translation of the Philadelphia chromosome into therapy for CML," *Blood*, vol. 112(13), pp. 4808-4817 (Dec. 15, 2008).
Legros et al., "Imatinib mesylate (STI571) decreases the vascular endothelial growth factor plasma concentration in patients with chronic myeloid leukemia," *Blood*, vol. 104(2), pp. 495-501 (Jul. 15, 2004).
Mayerhofer et al., "BCR/ABL induces expression of vascular endothelial growth factor and its transcriptional activator, hypoxia inducible factor-1α, through a pathway involving phosphoinositide 3-kinase and the mammalian target of rapamycin," *Blood*, vol. 100(10), pp. 3767-3775 (Nov. 15, 2002).
Office Action issued in Korean Patent Application No. 10-2011-7009183, dated Nov. 28, 2016.

* cited by examiner

INHIBITION OF PLGF TO TREAT PHILADELPHIA CHROMOSOME POSITIVE LEUKEMIA

CROSS-REFERENCE TO RELATED APPLICATIONS

This application is the U.S. National Phase under 35 U.S.C. § 371 of International Application PCT/EP2009/062861, filed Oct. 2, 2009, which claims priority to US Provisional Application No. 61/195,140, filed Oct. 2, 2008.

REFERENCE TO SEQUENCE LISTING

The present disclosure includes a sequence listing in Electronic format. The Sequence Listing is provided as a file entitled 27650818_1.txt, created Feb. 21, 2018, which is approximately 4 KB in size. The information in the electronic format of the sequence listing is incorporated herein by reference in its entirety.

FIELD OF THE INVENTION

The present application relates to the field of cancer, in particular leukemia. More in particular, it relates to treatment of Philadelphia chromosome positive (Ph+) leukemia. This is achieved via inhibition of placental growth factor (PlGF). Thus, methods are provided for treatment of Ph+ leukemia using PlGF inhibitors, in particular using an anti-PlGF antibody. A particular type of leukemia that is envisaged to be treated this way is chronic myelogenous leukemia (CML), especially also in patients where conventional BCR/ABL inhibitors, such as imatinib, fail to have sufficient therapeutic effect.

BACKGROUND

Philadelphia chromosome, also known as the Philadelphia translocation, is a specific chromosomal abnormality that is associated with chronic myelogenous leukemia (CML). It is the result of a reciprocal translocation between chromosome 9 and 22, and is specifically designated t(9; 22)(q34; q11). The presence of this translocation is a highly sensitive test for CML, since 95% of CML patients have this abnormality. The remaining 5% of CML patients typically have either a cryptic translocation that is invisible on G-banded chromosome preparations, or a variant translocation involving another chromosome or chromosomes as well as the long arm of chromosomes 9 and 22. However, the mere presence of the Philadelphia (Ph) chromosome is not sufficiently specific to diagnose CML, since it is also found in 25-30% of adult acute lymphoblastic leukemia (ALL) cases (and in 2-10% in pediatric ALL cases).

Nevertheless, these diseases are clearly distinct. Acute lymphoblastic leukemia (ALL) is a form of leukemia in which malignant, immature white blood cells continuously multiply and are overproduced in the bone marrow. ALL causes damage and death by crowding out normal cells in the bone marrow, and by spreading (metastasizing) to other organs. ALL is most common in childhood and young adulthood with a peak incidence at 4-5 years of age, and another peak in old age. The overall cure rate in children is 85%, and about 50% of adults have long-term disease-free survival. 'Acute' refers to the undifferentiated, immature state of the circulating lymphocytes ("blasts"), and to the rapid progression of disease, which can be fatal in weeks to months if left untreated. Treatment for acute leukemia can include chemotherapy, steroids, radiation therapy, intensive combined treatments (including bone marrow or stem cell transplants), and growth factors.

Chronic myelogenous (or myeloid) leukemia (CML) on the other hand is a form of leukemia characterized by the increased and unregulated growth of predominantly myeloid cells in the bone marrow and the accumulation of these cells in the blood; it is thus a myeloproliferative disease. CML is a clonal bone marrow stem cell disorder in which proliferation of mature granulocytes (neutrophils, eosinophils, and basophils) and their precursors is the main finding. Historically, it has been treated with chemotherapy, interferon and bone marrow transplantation, although targeted therapies are now also available and used as standard of care.

The swapping of parts of chromosomes 9 and 22 observed in the Philadelphia chromosome gives rise to a BCR-ABL fusion gene (Melo, 1996). That is to say, part of the BCR ("breakpoint cluster region") gene from chromosome 22 (region q11) is fused with part of the ABL gene on chromosome 9 (region q34). Abl stands for "Abelson", the name of a leukemia virus which carries a similar protein. Two kinds of BCR-ABL transcripts (which yield p185 and p210 isoforms, named after their apparent molecular weight in kDa) are generated due to the breakpoint of the BCR region. The fused "BCR-ABL" gene is located on the resulting, shorter chromosome 22. ABL carries a domain that can add phosphate groups to tyrosine residues (a tyrosine kinase), and the BCR-ABL fusion gene product is also a tyrosine kinase (Faderl et al., 1999).

The fused BCR-ABL protein interacts with the interleukin-3 β common receptor subunit. The BCR-ABL transcript is continuously active and does not require activation by other cellular messaging proteins. In turn, BCR-ABL activates a cascade of proteins which control the cell cycle, speeding up cell division. Moreover, the BCR-ABL protein inhibits DNA repair, causing genomic instability and making the cell more susceptible to developing further genetic abnormalities, and potentially promoting progression of CML from chronic phase towards untreatable blast crisis. The tyrosine kinase action of the BCR-ABL protein is believed to be the pathophysiologic cause of chronic myelogenous leukemia. Targeted therapies specifically inhibiting the activity of the BCR-ABL protein have been developed. The first of these was imatinib (marketed as its mesylate salt under the trade name Glivec® or Gleevec®). These and other tyrosine kinase inhibitors can induce complete remissions in CML, confirming the central importance of BCR-ABL in CML (Hehlmann et al., 2007). Limited success was also reported when treating Philadelphia chromosome positive (Ph+) ALL with BCR-ABL inhibitors (Yanada and Naoe, 2006; Piccaluga et al., 2006).

Despite the fact that introduction of imatinib and second-generation BCR/ABL inhibitors (e.g. dasatinib) has revolutionized treatment of patients with Philadelphia chromosome positive (Ph+) leukemias, it is a known problem that leukemia cells persist even in successfully treated patients, and some patients develop resistance and ultimately relapse (Swords et al., 2007; Buchert, 2007; Li and Li, 2007; Kujawski and Talpaz, 2007). The reasons for these drawbacks are not entirely resolved.

Thus, it would be advantageous to have further options to treat patients with Philadelphia chromosome positive leukemia, particularly those patients not responsive to treatment with BCR-ABL inhibitors.

SUMMARY OF THE INVENTION

It is an object of the application to provide novel therapeutic approaches to treat Philadelphia chromosome positive (Ph+) leukemias. Particularly, it is envisaged to also be able to provide approaches helpful to those patients where BCR-ABL inhibitors, like imatinib, are not (or not anymore) suited as therapy. Surprisingly, it was found that inhibition of placental growth factor (PlGF), even though this factor is not expressed in leukemia cell lines, results in significantly prolonged survival of leukemic mice. Moreover, this prolonged survival is independent of BCR-ABL mutational status, contrary to what is seen for BCR-ABL inhibitors.

Thus, according to a first aspect, the use of an inhibitor of placental growth factor for the treatment of Philadelphia chromosome positive leukemia is envisaged. Also envisaged is the use of an inhibitor of placental growth factor for the preparation of a medicament for the treatment of Philadelphia chromosome positive leukemia.

Likewise, methods are provided for treating Philadelphia chromosome positive leukemia in a subject in need thereof, comprising administering an inhibitor of PlGF to the subject. Of course, it is the goal to thereby ameliorate the symptoms or ultimately treat the Ph+ leukemia in the subject in need thereof.

According to particular embodiments, the inhibitor of placental growth factor provided in the uses and methods described herein is a selective inhibitor of placental growth factor. Particularly, the selective inhibitor is an antibody or a fragment thereof specifically binding to placental growth factor. Such antibody may be a monoclonal or polyclonal antibody. According to particular embodiments, the antibody or a fragment thereof specifically binding to placental growth factor is a monoclonal antibody. According to further particular embodiments, it is a murine monoclonal antibody. According to still further particular embodiments, murine monoclonal antibodies may be humanized, i.e. humanized versions of the mouse monoclonal antibodies made by means of recombinant DNA technology, starting from the mouse and/or human genomic DNA sequences coding for H and L chains or from cDNA clones coding for H and L chains. According to alternative embodiments, the antibody or fragment thereof is a human antibody (or fragment thereof), in particular a human monoclonal antibody.

According to particular embodiments, the fragment of the antibody specifically binding to PlGF is a Fab fragment, a F(ab')2 fragment or a single chain variable fragment (scFv).

According to alternative particular embodiments, the selective inhibitor is a nanobody against PlGF.

According to yet other particular embodiments, the PlGF inhibitor is not a selective inhibitor. A particular example thereof is a VEGFR-1 inhibitor, such as a VEGFR-1 antibody or a fragment thereof.

Methods and uses of PlGF inhibitors are provided for the treatment of Philadelphia chromosome positive (Ph+) leukemias. According to particular embodiments, the Philadelphia chromosome positive leukemia is chronic myelogenous leukemia (CML). According to alternative embodiments, the Ph+ leukemia is acute lymphoblastic leukemia (ALL), such as e.g. B-ALL (in which B cells are leukemic cells) or T-ALL (in which the leukemia cells are T cells).

It is envisaged that the methods and uses described herein have broad applicability. In particular, it is envisaged that PlGF inhibitors can be used for treatment (or in methods of treatment) of all Philadelphia chromosome positive leukemias, in particular also those that cannot be treated with a BCR-ABL inhibitor and/or those that cannot be treated with a BCR-ABL inhibitor alone. A Ph+ leukemia may not be treatable with a BCR-ABL inhibitor—or a BCR-ABL inhibitor alone—for a variety of reasons. The most common reasons are that the leukemia may be (at least partially) insensitive to the treatment (or have developed an at least partial resistance/insensitivity to the treatment), or that the BCR-ABL inhibitor may not be tolerated by the patient (e.g. due to allergy or adverse side effects). While PlGF inhibition offers a general approach in the treatment of Ph+ leukemias, it may be especially beneficial for those cases where BCR-ABL inhibition, a standard therapeutic approach for e.g. CML, fails to lead to the desired therapeutic effect. The use of PlGF inhibitors may then offer an alternative or additional approach. According to specific embodiments, the PlGF inhibitor may be used in combination with a BCR-ABL inhibitor.

DETAILED DESCRIPTION

Definitions

Figure 1:
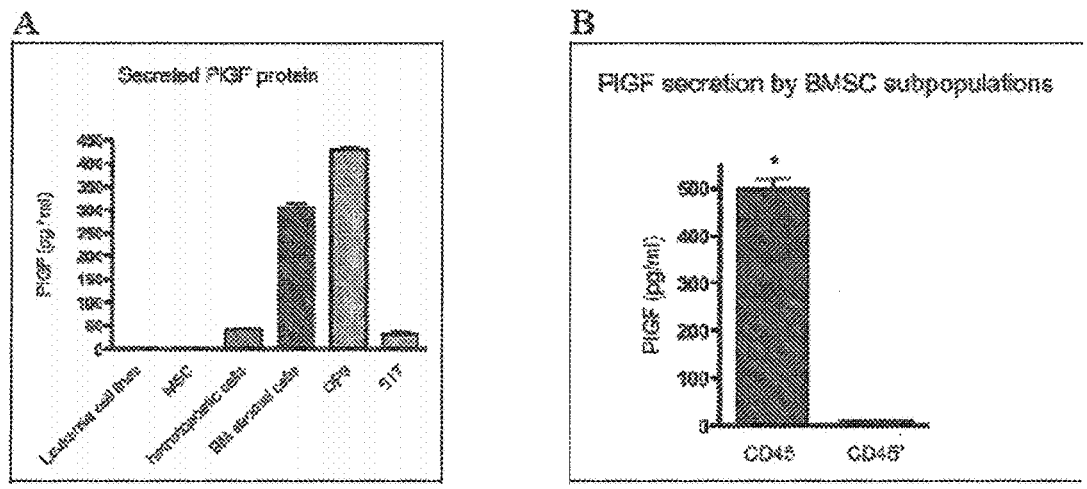
FIG. 1 shows PlGF expression in leukemia cells, hematopoietic cells and primary bone marrow stromal cells in vitro. A: amount of secreted PlGF protein by different cell lines and isolated cells (see Example 1 for more details); B: PlGF expression by the hematopoietic fraction (CD45$^+$) and non-hematopoietic fraction (CD45$^-$) of murine BMDSCs. * indicates p<0.001. BM: bone marrow.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

"Placental growth factor" or "PlGF" as used herein refers to a member of the VEGF (vascular endothelial growth factor) sub-family, in particular the human PlGF (GeneID 5228; RefSeqs (independently of genome builds) NM_002632.4 (mRNA) and NP_002623.2 (protein)). Unless otherwise specified, the term "PlGF" may refer to the gene as well as its products, such as the PlGF RNA (most particularly, the PlGF mRNA) and the PlGF protein. All isoforms of PlGF are intended to be included in the definition of PlGF.

The term "Philadelphia chromosome positive" or "Ph+" leukemia as used herein refers to diseases wherein the Philadelphia translocation is confirmed to be present. The Philadelphia chromosome is a result of the t(9; 22)(q34; q11) translocation (Philadelphia translocation). At least two alternative forms of the Philadelphia chromosome translocation are documented, but both alternative breakpoints result in the joining of different exon sets of BCR (OMIM *151410) on chromosome 22 to a common subset of the exons of the ABL gene (OMIM *189980) located on chromosome 9. Thus, the fusion may results in 2 alternative chimeric oncogene products called p210 (BCR-ABL) and p185 (BCR-ABL), herein collectively referred to as "BCR-ABL" (included in OMIM *151410 and *189980). The activation of ABL tyrosine kinase activity is necessary for the oncogenic potential of the chimeric oncogene. As the presence of the chimeric BCR-ABL gene (and its gene products) is a hallmark of Ph+ leukemias, "Ph+" may also be referred to as "BCR-ABL positive" or "BCR-ABL+" leukemias, to indicate the presence of the fusion gene. Note that translocations or mutations which result in the generation of a functional BCR-ABL chimeric gene (i.e. BCR-ABL+) will herein thus also be classified as "Ph+", regardless of the mechanism of the translocation. This may for instance be the case with more complex translocations.

A "selective inhibitor of placental growth factor" as used in the application is a molecule or compound that inhibits the function or signaling pathway of PlGF without interfering with the physiological function of other molecules. In particular, a selective PlGF inhibitor will not interfere with the function of VEGF. Thus, as a non-limiting example, a compound specifically directed against PlGF (e.g. an anti-PlGF antibody) is a selective inhibitor, while compounds that also target VEGF (such as VEGFR1-based compounds) or target VEGF/PlGF-shared receptors (e.g. an antibody against VEGFR1, or sVEGFR-1) is typically a non-selective inhibitor.

"Chronic myelogenous leukemia", "chronic myeloid leukemia" or "CML" as used herein refers to a clonal myeloproliferative disorder of a pluripotent stem cell with a specific cytogenetic abnormality (the Philadelphia chromosome), involving myeloid, erythroid, megakaryocytic, B lymphoid, and sometimes T lymphoid cells, but not marrow fibroblasts (OMIM #608232; Silver, 2003).

"Acute lymphocytic leukemia", "acute lymphoblastic leukemia" or "ALL" as used in the application refers to an acute form of leukemia in which immature white blood cells continuously multiply and are overproduced in the bone marrow. Examples of ALL include T-ALL and B-ALL. A particular subset of the heterogeneous group of ALL cases also is positive for the Philadelphia chromosome, i.e. Ph+ or BCR-ABL+ (Radich, 2001; Alvarado et al., 2007).

As used in the application, a "BCR-ABL inhibitor" is a molecule or compound that inhibits the expression or function of the chimeric BCR-ABL gene or its gene product. Of note, the BCR-ABL inhibitor need not necessarily be specific for BCR-ABL. For instance, it may be a tyrosine kinase inhibitor which targets more than just the BCR-ABL tyrosine kinase. A BCR-ABL inhibitor is well-known as a targeted therapy in Ph+ leukemia, a non-limiting but typical example is imatinib. Other examples are included in the application.

"Treating" as used in the application means to achieve a significant amelioration of one or more clinical symptoms associated with Ph+ leukemia. Depending on the situation, the significant amelioration may be scored quantitatively or qualitatively. Qualitative criteria may e.g. be patient well-being. In the case of quantitative evaluation, the significant amelioration is typically a more than 10%, more than 20%, more than 25%, more than 30%, more than 40%, more than 50%, more than 60%, more than 70%, more than 75%, more than 80%, more than 90%, more than 95%, or a 100% or more improvement over the situation prior to administration of the PlGF inhibitor. Of course, if improvement is expressed as a decrease (e.g. the number of malignant cells present in a patient sample), improvement cannot be more than 100%. The time-frame over which the improvement is evaluated will depend on the type of criteria observed and can be determined by the person skilled in the art.

It is an important aspect of the invention to provide methods and uses of inhibitors of placental growth factor for the treatment of Philadelphia chromosome positive leukemia. Also, the use of inhibitors of placental growth factor for the manufacture of a medicament for the treatment of Philadelphia chromosome positive leukemia is taught.

Inhibitors of placental growth factor (PlGF) particularly are selective inhibitors of PlGF, so as not to interfere with other molecules. In particular, the selective PlGF inhibitors should not interfere with the function of VEGF. According to particular embodiments, the PlGF inhibitor is not a VEGF inhibitor.

According to alternative particular embodiments, the PlGF inhibitor is not a VEGFR1 inhibitor. According to specific embodiments, the PlGF inhibitor is not based on the VEGFR1.

Inhibitors may neutralize the activity of PlGF by interfering with its synthesis, translation, dimerisation, receptor-binding and/or receptor-binding-mediated signal transduction. Neutralizing the activity of PlGF should be understood as suppressing the PlGF activity for at least 20%, 30%, 40%, 50%, 60%, 70%, 80%, 90% or even 100%.

Inhibitors, in particular selective inhibitors, of PlGF are known in the art. According to particular embodiments, the selective inhibitors are antibodies. The term "antibody" or "antibodies" relates to an antibody characterized as being specifically directed against PlGF or any functional derivative thereof or an antigen-binding fragment thereof, particularly of the F (ab') 2, F (ab) or single chain Fv (scFv) type, or any type of recombinant antibody derived thereof. The anti-PlGF antibodies described herein, including specific polyclonal antisera prepared against PlGF or any functional derivative thereof, have no cross-reactivity to others proteins. According to particular embodiments, the anti-PlGF antibodies are monoclonal antibodies. The monoclonal antibodies can for instance be produced by any hybridoma liable to be formed according to classical methods from splenic cells of an animal, particularly of a mouse or rat immunized against PlGF or any functional derivative thereof, and of cells of a myeloma cell line, and to be selected by the ability of the hybridoma to produce the monoclonal antibodies recognizing PlGF or any functional derivative thereof which have been initially used for the immunization of the animals.

According to particular embodiments, preparing monoclonal antibodies against human PlGF can for instance be done as follows: a recombinant human PlGF fusion protein, consisting of the amino acids encoded by PlGF or a fragment thereof is coupled to Glutathione S-transferase (GST) and expressed in *Escherichia coli* and purified by affinity chromatography on immobilised glutathione (Amersham Biosciences). Recombinant human PlGF is also obtainable from R&D Systems Inc. 614 McKinley Place N. E. Minneapolis, Minn. 55413, USA. (264-PG-010, 264-PG-010/CF, 264-PG-050 or 264-PG-050/CF), from Research Diagnostics Inc, Pleasant Hill Road, Flanders N.J. 07836, USA (Recombinant Human PlGF-1: Cat#RDI-300-015 & Cat#RDI-300-016 and Recombinant Human PlGF-2: Cat#RDI-300-019) or from ALEXIS Corporation, CH-4415 Lausanne, Switzerland (Placenta Growth Factor-2 (human) (recombinant) cat#RLT-300-020).

Recombinant human PLGF is mixed with an equal amount of an adjuvant, and an obtained mixture is then subcutaneously administrated to Balb/c male mice (8 weeks old upon the start of immunisation) in an amount corresponding to an amount of PlGF of 100 μg per 1 mouse (priming immunisation).

After about 21 days, immunisation can be performed by subcutaneous administration in the same manner as described above (booster immunisation). After 19 days or 30 days from the booster, the mice can administrated through their tail veins with 200 μl of a preparation obtained by diluting human PlGF with PBS (phosphate-buffered physiological saline) to have a concentration of 250 μg/ml (final immunisation). Spleens have then to be excised from the mice after about 3 days from the final immunisation, and they have to be separated into single cells. Subsequently, the spleen cells should be washed with a proper medium, e.g. DMEM medium. On the other hand, suitable mouse myeloma cells (e. g. Sp2/0-Ag14) have to be collected in the logarithmic growth phase, and to be washed with a proper medium, e.g. DMEM medium. The spleen cells and the mouse myeloma cells have to be sufficiently mixed in a plastic tube in a ratio of numbers of the cells of 10:1, followed by addition of 50% (w/v) polyethylene glycol (PEG e.g. of Boehringer Mannheim, average molecular weight: 4000) to perform cell fusion at 37° C. for 7 minutes. After removal of the supernatant solution (by means of centrifugation), the residue is added with HAT medium (DMEM medium containing 10% fetal bovine serum added with hypoxanthine, aminopterin, and thymidine). The residue has to be suspended so that a concentration of the spleen cells of about $5 \times 10^6$ cells/ml is obtained. This cell suspension can then be dispensed and poured into 96-well plastic plates so that one well contains about 100 μl of the suspension, followed by cultivation at 37° C. in 5% carbon dioxide. HAT medium has to be supplemented; for instance in an amount of 50 μl/well on $2^{nd}$ and $5^{th}$ days. After that, half volume of the medium can be exchanged every 3 or 4 days in conformity with proliferation of hybridomas.

Hybridomas, which produce the monoclonal antibody of the present invention, have to be screened for. This has to be done by using, as an index, the inhibitory activity of the monoclonal antibody on the physiological activity possessed by PlGF.

Hybridomas which produced monoclonal antibodies exhibiting reactivity with PlGF have then to be selected from the selected clones. The obtained hybridomas have then to be transferred to a suitable medium for instance HT medium which is the same as HAT medium, but without aminopterin, and cultured further. Cloning can be performed twice in accordance with the limiting dilution method by which stable hybridomas are obtainable.

Production and purification of monoclonal antibodies may then be done as follows: 2,6, 10, 14-Tetramethylpentadecane (e. g. Pristane of Sigma, 0.5 ml) can be intraperitoneally injected into Balb/c female mice (6 to 8 weeks old from the birth). After 10 to 20 days, cells of clones ($1 \times 10^6$ to $10^7$ cells) can be suspended in PBS and intraperitoneally inoculated into the mice. After 7 to 10 days, the mice can be sacrificed and subjected to an abdominal operation, from which produced ascitic fluid can be collected. The ascitic fluid can be centrifuged to remove insoluble matters, and a supernatant was recovered and stored at $-20°$ C. until purification. Consequently, IgG can be purified from the ascitic fluid supernatant described above by using Hi-Trap Protein-A antibody purification kit (available from Pharmacia, Roosendaal, Netherlands). Namely, the ascitic fluid (2 ml) can be added with Solution A (1.5 M glycine, 3 M NaCl, pH 8.9, 8 ml), and filtrated with a filter for filtration having a pore size of 45 ml (Millipore). After that, an obtained filtrate can applied to a column (column volume: 1 ml) charged with Protein Sepharose HP (produced by Pharmacia) sufficiently equilibrated with Solution A, and the column has be washed with Solution A in an amount of 10-fold column volume. Subsequently, an IgG fraction can be eluted with Solution B (0.1 M glycine, pH 2.8) in an amount of 10-fold column volume. The eluted IgG fraction can be dialysed against PBS. The monoclonal antibodies can be determined for their IgG subclasses by using the purified antibodies obtained in the foregoing, by means of a commercially available subclass-determining kit (trade name: Mono Ab-ID EIA Kit A, produced by Zymed). This method is based on the ELISA method.

The inhibitory activities of monoclonal antibodies can be tested for complete inhibition of binding of rPlGF to its VEGFR1 receptor. This can for instance be measured in an immunofunctional ELISA in which 96-well plates are coated with 100 μl of 1 μg/ml of rmFlt-l/Fc chimera overnight at room temperature in PBS. After blocking for 1 hour with 1% BSA in PBS, 100 μl of a mixture of 70 μl of hybridoma medium pre-incubated with 70 μl of recombinant mPlGF-2 at 10 ng/ml for 2 hours at room temperature is then applied to the plate. A standard of rmPlGF-2 ranging from 20 ng/ml to 156 pg/ml can be included (diluted in PBS-Tween. BSA-EDTA). Plates can then be incubated 1 hour at 37° C. and 1 hour at room temperature, washed 5 times with PBS-Tween and 100 μl of biotinylated goat anti-murine PlGF-2 at 200 ng/ml can be applied for 2 hours at room temperature. After washing 5 times with PBS-Tween, 100 μl of avidin-HRP conjugate (Vectastorin ABC kit) can be applied for 1 hour at room temperature. After washing 5 times with PBS-Tween, the plate can be developed with 90 μl of o-phenylene diamine in citrate phosphate buffer pH 5.0 for 30 minutes and measured at 490 nm.

Also provided herein are inhibiting antibody ligands, which are able to bind to PlGF. More preferably, such a ligand should be able to recognise a specific epitope located on PlGF. For instance, the present invention relates to ligands of the above-mentioned type, being derived from a monoclonal antibody produced by on purpose immunisation in animals. The present invention also provides an antigen-binding Fab fragment, or a homologue derivative of such fragment, which may be obtained by proteolytic digestion of the said monoclonal antibody by papain, using methods well known in the art. In order to reduce the immunogenicity of the murine anti-PlGF monoclonal antibody, the present invention also includes the construction of a chimeric antibody, preferentially as a single-chain variable domain, which combines the variable region of the mouse antibody with a human antibody constant region—a so-called humanised monoclonal antibody.

The monoclonal antibodies produced in animals may be humanised, for instance by associating the binding complementarily determining region ("CDR") from the non-human monoclonal antibody with human framework regions—in particular the constant C region of human gene—such as disclosed by Jones et al. (Jones et al., 1986) or Riechmann (Riechmann et al., 1988), or otherwise hybridised.

The monoclonal antibodies according to these embodiments may be humanized versions of the mouse monoclonal antibodies made by means of recombinant DNA technology, departing from the mouse and/or human genomic DNA sequences coding for H and L chains or from cDNA clones coding for H and L chains.

Alternatively the monoclonal antibodies according to these embodiments may be human monoclonal antibodies. Such human monoclonal antibodies are prepared, for instance, by means of human peripheral blood lymphocytes (PBL) repopulation of severe combined immune deficiency (SCID) mice as described in PCT/EP99/03605 or by using transgenic non-human animals capable of producing human antibodies as described in U.S. Pat. No. 5,545,806. Also fragments derived from these monoclonal antibodies such as Fab, F (ab')2 and scFv ("single chain variable fragment"), providing they have retained the original binding properties, form part of what is disclosed herein. Such fragments are commonly generated by, for instance, enzymatic digestion of the antibodies with papain, pepsin, or other proteases. According to particular embodiments, the selective inhibitor of PlGF is a fragment of an antibody, which fragment specifically binds to placental growth factor. According to particular embodiments, the antibody fragment is a Fab fragment, a F(ab')2 fragment or a single chain variable fragment (scFv).

According to specific embodiments, preparing of F (ab') 2 or monovalent Fab fragments is for instance as follows: in order to prepare F (ab') 2 fragments, the monoclonal antibody can be dialysed overnight against a 0.1 mol/L citrate buffer (pH 3.5). The antibody (200 parts) is then digested by incubation with pepsin (1 part) available from Sigma (Saint-Louis, Mo.) for 1 hour at 37° C. Digestion is consequently stopped by adding 1 volume of a 1 M Tris HCl buffer (pH 9) to 10 volumes of antibody. Monovalent Fab fragments can be prepared by papain digestion as follows: a 1 volume of a 1M phosphate buffer (pH 7.3) is added to 10 volumes of the monoclonal antibody, then 1 volume papain (Sigma) is added to 25 volumes of the phosphate buffer containing monoclonal antibody, 10 mmol/l L-Cysteine HCl (Sigma) and 15 mmol/l ethylene diaminetetra-acetic acid (hereinafter referred to as EDTA). After incubation for 3 hours at 37° C., digestion is stopped by adding a final concentration of 30 mmol/l freshly prepared iodoacetamide solution (Sigma), keeping the mixture in the dark at room temperature for 30 minutes. Both F (ab') 2 and Fab fragments can further be purified from contaminating intact IgG and Fc fragments using protein-A-Sepharose. The purified fragments can finally dialysed against phosphate-buffered saline (herein after referred as PBS). Purity of the fragments can be determined by sodiumdodecylsulphate polyacrylamide gel electrophoresis and the protein concentration can be measured using the bicinchonicic acid Protein Assay Reagent A (Pierce, Rockford, Ill.).

It is well known to the person skilled in the art that (monoclonal) antibodies, or fragments thereof, can be modified for various uses. The antibodies involved in the invention can be labeled by an appropriate label of the enzymatic, fluorescent, or radioactive type.

Examples of anti-PlGF antibodies are well documented in the art. They include, but are not limited to the one described by Fischer (Fischer et al., 2007), or the murine monoclonal antibody Mab-PL5DII (WO01/85796; this monoclonal antibody is available in the VIB Vesalius Research Center, UZ Gasthuisberg, Herestraat 49, B-3000 Leuven). Other antibodies, such as the 16D3 antibody, as produced by the cell line deposited as LM BP 6399CB with the BCCM/LMBP (Belgian Co-ordinated Collections of Microorganisms/Plasmid Collection Laboratorium voor Moleculaire Biologie, University of Ghent K.L. Ledeganckstraat 35, B-9000 Ghent, BE), are for instance described in EP1869085. As disclosed in EP1869085, the CDR regions within the variable regions of 16D3 correspond to SEQ ID NO: 1 (GYTFTDYY), SEQ ID NO: 2 (IYPGSGNT); SEQ ID NO: 3 (VRDSPFFDY), SEQ ID NO: 4 (QSLLNSGMRKSF), SEQ ID NO: 5 (WASXaa) and SEQ ID NO: 6 (KQSYHLFT). Also, as disclosed in EP1869085, the 16D3 variable regions of heavy and light chain sequences correspond to SEQ ID NO: 10 and 11. As disclosed in EP1869085, the nucleotide sequences encoding the variable heavy chain region and the light chain region variable region defined by SEQ ID NO: 10 and SEQ ID NO: 11, respectively, are SEQ ID NO: 7 and SEQ ID NO: 8, corresponding to the sequences encoding the heavy and light chain region of antibody 16D3. As disclosed in EP1869085, the 16D3 scFV sequence corresponds to SEQ ID NO: 9. As disclosed in EP1869085, the sequence of the humanized 16D3 variable regions of the heavy chain and light chain correspond to SEQ ID NO: 10 and 11. As disclosed in EP1869085, the humanized 16D3 scFV sequence corresponds to SEQ ID NO: 12. Also WO2004/002524 describes how to generate anti-PlGF antibodies. Both EP1869085 and WO2004/002524 are hereby incorporated by reference. Moreover, anti-PlGF antibodies are also commercially available, e.g. from Santa Cruz Biotechnology Inc, Abcam, Novus biologicals, R&D systems, Sigma-Aldrich and many more companies.

It is to be understood that the above methods also apply for the generation of other antibodies, e.g. for the generation of anti-VEGFR-1 antibodies, which are non-selective inhibitors of PlGF.

Other inhibitors of PlGF, particularly selectively inhibitors of PlGF, include, but are not limited to, peptides, tetrameric peptides, proteins, organic molecules, or fragments or homologues thereof having neutralizing effect as stated above. Further inhibitors in this non-exhaustive list are anti-sense RNA and DNA molecules and ribozymes that function to inhibit the translation of PlGF, peptide aptamers (e.g., siRNAs (e.g. Santa Cruz Biotechnology Inc), hairpin RNAs or shRNAs (e.g. Santa Cruz Biotechnology Inc), morfolinos, nanobodies and small molecules. Many of such (selective as well as non-selective) inhibitors are commercially available. Some of the possible inhibitors will be further discussed here.

Small molecules, e. g. small organic molecules, and other drug candidates can be obtained, for example, from combinatorial and natural product libraries. To screen for said candidate/test molecules, for instance cell lines that express VEGFR-1 may be used and the signal transduction is monitored as described in detail in WO 01/85796 which is herein incorporated by reference.

Said monitoring can be measured using standard biochemical techniques. Other responses such as activation or suppression of catalytic activity, phosphorylation (e. g. the tyrosine phosphorylation of the intracellular domain of the receptor) or dephosphorylation of other proteins, activation or modulation of second messenger production, changes in cellular ion levels, association, dissociation or translocation of signaling molecules, or transcription or translation of specific genes may also be monitored. These assays may be performed using conventional techniques developed for these purposes in the course of screening. Inhibition of ligand binding to its cellular receptor may, via signal transduction pathways, affect a variety of cellular processes. Cellular processes under the control of the VEGFR-1/PlGF signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

An alternative way of screening for small molecules is via in silico design. The crystal structure of human Placental growth factor is available (PDB Code: 1FZV), so this may also serve as a platform for further small molecule antagonist screens. An inhibitory molecule or series of molecules can be designed based on the structure of PlGF, after which they can be validated using screens as described above.

Random peptide libraries, such as tetrameric peptide libraries further described herein, consisting of all possible combinations of amino acids attached to a solid phase support may be used to identify peptides that are able to bind to the ligand binding site of a given receptor or other functional domains of a receptor such as kinase domains (Lam et al., 1991). The screening of peptide libraries may have therapeutic value in the discovery of pharmaceutical agents that act to inhibit the biological activity of receptors through their interactions with the given receptor. Identification of molecules that are able to bind to PlGF (or optionally the VEGFR-1) may be accomplished by screening a peptide library with recombinant PlGF protein (or soluble VEGFR-1 protein). For example, the kinase and extracellular ligand binding domains of VEGFR-1 may be separately expressed and used to screen peptide libraries. In addition to using soluble VEGFR-1 molecules, in another embodiment, it is possible to detect peptides that bind to cell surface receptors using intact cells. The cells used in this technique may be either alive or fixed cells. The cells will be incubated with the random peptide library and will bind certain peptides in the library to form a "rosette" between the target cells and the relevant solid phase support/peptide. The rosette can thereafter be isolated by differential centrifugation or removed physically under a dissecting microscope.

In a specific embodiment transdominant-negative mutant forms of VEGF-receptors (e.g. a transdominant-negative receptor of VEGF-R1) can be used to inhibit the signal transduction of PlGF. The use of said transdominant-negative mutant forms of VEGF-receptors is fully described in U.S. Pat. No. 5,851,999. Moreover, the placenta soluble fms-like tyrosine kinase 1 (sFlt1), a splice variant of the VEGF receptor Flt1 lacking the transmembrane and cytoplasmic domains, is known to act as a potent PlGF antagonist (Kendall et al., 1996; Shibuya, 2001) and soluble VEGFR1 fusion proteins (Aiello et al., 1995) can be used in vivo to inhibit PlGF activity. However, although successful in its own right, the use of transdominant-negative receptors may have the drawback of not being selective inhibitors of PlGF alone. Thus, according to specific embodiments, the inhibitor of PlGF is not a transdominant-negative receptor.

RNA has distinct advantages over small organic molecules when considering its use to inactivate protein function in vivo. An RNA encoding sequence can be linked to a promoter and this artificial gene can be introduced into cells or organisms. Depending on the regulatory sequence included, this provides a unique way of constructing a time—and/or tissue-specific suppressor gene. Such RNA expressing genes are usually smaller than protein-coding genes and can be inserted easily into gene therapy vectors. Unlike a foreign or altered protein, RNA is less likely to evoke an immune response. Antisense molecules and ribozymes have been developed as "code blockers" to inactivate gene function, with their promise of rational drug design and exquisite specificity (Altman, 1995; Matteucci and Wagner, 1996). Mechanistically, both antisense oligodeoxynucleotides ("ODNs") and bioengineered ribozymes are expected to achieve specific binding in the first step of their action by forming a stable duplex (or triplex in some cases of the ODNs) with a target nucleotide sequence based on Watson-Crick or Hoogsteen base pairing.

In certain embodiments, a PlGF inhibitor may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In particular embodiments, the PlGF-binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR 2, P(O)R, P(O)OR', CO, or CNR 2, wherein R is H or alkyl (1-20 C) and R' is alkyl (1-20 C); in addition, this group may be attached to adjacent nucleotides through O or S. Not all linkages in an oligomer need to be identical.

The aptamers used as starting materials to determine specific binding sequences may be single-stranded or double-stranded DNA or RNA. In a particular embodiment, the sequences are single-stranded DNA, which is less susceptible to nuclease degradation than RNA. According to particular embodiments, the starting aptamer will contain a randomized sequence portion, generally including from about 10 to 400 nucleotides, particularly from 20 to 100 nucleotides. The randomized sequence is flanked by primer sequences that permit the amplification of aptamers found to bind to the target. For synthesis of the randomized regions, mixtures of nucleotides at the positions where randomization is desired may be added during synthesis.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) are retained during separation. Each cycle results in an enrichment of aptamers with high affinity for the target. Repetition for between three to six selection and amplification cycles may be used to generate aptamers that bind with high affinity and specificity to the target, such as PlGF.

According to particular embodiments, the aptamers are RNA aptamers which specifically interact with PLGF, or optionally with VEGF-R1 or other non nucleic acid substances of the VEGFR-1/PlGF signalling pathway. These can be used as therapeutic reagents. RNA aptamers are used for their ability directly to disrupt protein function. Selection of aptamers in vitro allows rapid isolation of extremely rare RNAs that have high specificity and affinity for specific proteins. Exemplary RNA aptamers are described in U.S. Pat. No. 5,270,163 to Gold et al., and papers by Ellington and Szostak, 1990, and Tuerk and Gold, 1990. Unlike antisense compounds, whose targets are one dimensional lattices, RNA aptamers can bind to the three dimensional surfaces of a protein. Moreover, RNA aptamers can frequently discriminate finely among discrete functional sites of a protein (Gold et al., 1995). As therapeutic reagents, aptamers not only have the combined advantages of antibodies and small molecular mass drugs, but in vivo production of RNA aptamers also can be controlled genetically. The controlled expression of high affinity RNA aptamers offers a means of rapidly inactivating specific domains of proteins and thereby assessing their function and mechanism of action.

Toole et al in U.S. Pat. No. 5,840,867 and Grossman et al in U.S. Pat. No. 6,207,388 disclose methods for making aptamers and aptamers that bind to biomolecules. These aptamers can be used to interfere with the normal biological function of the biomolecules, as a separation tool, a diagnostic or a therapeutic. The aptamers described by Toole et al. can be single chain or duplex RNA or DNA.

Korth et al. (Korth et al., 1997) have applied single-stranded RNA aptamers directed against Syrian golden hamster prion protein and the aptamers were able to recognise their specific target within a mixture of hundreds of different proteins. Davis (1994) described single-stranded DNA aptamer that binds the active site of thrombin and exhibits anti-coagulation effects in vivo.

Rajendran, Manjula et al. (US20020127581) provide methods for the in vitro selection of signaling aptamers comprising the steps of synthesising a DNA pool, the DNA having a random insert of nucleotides of a specific skewed mole ratio; amplifying the DNA pool; transcribing an RNA pool from the amplified DNA using a fluorescently labelled nucleotide; applying the fluorescently labelled RNA pool to an affinity column to remove the high-affinity fluorescent RNA molecules from the fluorescently labelled RNA pool; obtaining a cDNA pool from the high-affinity fluorescent RNA molecules; repeating the amplification and selection steps on the fluorescent RNA molecules and cloning the fluorescent RNA molecules to yield signaling aptamers. Signaling aptamers comprising DNA molecules are also selected for.

Also provided herein is a signaling aptamer that transduces the conformational change upon binding a ligand to a change in fluorescence intensity of the signaling aptamer.

Aptamers can thus be designed to interact specifically with non-nucleic acid substances, such as PlGF or VEGFR1. Aptamers can function as high affinity receptors for PlGF or can tightly interact with PlGF (or optionally VEGFR1). The folding of an initially unstructured molecule around PLGF or VEGFR1 and forming a hydrogen-bond network with PLGF or VEGFR1 facilitate this neutralising binding.

Aptamers can however also be catalytic. Aptamers that are catalytic are considered approximate ribozymes, or aptazymes. Aptamers can as well be designed to interact specifically with nucleic acid substances, other than to simply bind them on the basis of Watson-Crick base pairing between bases in nucleic acid sequences of opposite orientation.

Such aptamers, if catalytic, may be fairly called aptazymes. Such specific action can be sought for therapeutic purposes.

The production of 2'-Fluoropyrimidine RNA-based aptamers to the 165-amino acid form of vascular endothelial growth factor (VEGF165), a protein with 53% sequence homology to PlGF, have been described in detail by Ruckman et al., 1998 and Bridonneau et al., 1999. Using the SELEX process (described above, US patent by Gold et al.) 2'-F-pyrimidine RNA oligonucleotide ligands (aptamers) to human VEGF165 were isolated. These aptamers also bound to the heterodimers of VEGF165 and PlGF123 and likely also to larger isoforms such as the isoform PlGF152. Representative aptamers from three distinct sequence families were truncated to the minimal sequence capable of high affinity binding to VEGF (23-29 nucleotides) and were further modified by replacement of 2'-O-methyl for 2'-OH at all ribopurine positions where the substitution was tolerated. This protocol can be used by a man skilled in the art to manufacture neutralising anti-PlGF aptamers. A VEGF aptamer (Macugen®, pegaptanib sodium) is also the first therapeutic aptamer to be administered to humans and is currently being marketed for patients with age-related macular degeneration.

Also within the scope of inhibitors as described herein are oligoribonucleotide sequences, that include catalysing RNA molecules such as ribozymes that function to inhibit the translation of VEGFR-1 mRNA or PlGF mRNA.

A number of RNA molecules are known to be active as catalysts and do not merely serve as the means by which information is moved out of the nucleus.

Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic cleavage. The activity of self-cleaving or cleaving other RNA of ribozymes is understood to be dependent on the RNA's secondary structure, which can be dependent on factors such as base sequence and the inclusion of metal locations. Ribozymes have great utility in artificially controlling gene expression. Advantage can be taken of the very specific charge patterns of nucleic acids, their bases and backbones and DNA's ability to form predictable secondary structure, based upon base sequence and predictable Watson-Crick base pairing. The small dimensions and flexible nature of nucleic acid make it well suited for constructing complexes capable of recognising and specifically binding to features on other substances, such as proteins. Through SELEX-driven screening (U.S. Pat. No. 5,567, 588 to Gold et al.), which depends upon binding to single-stranded nucleic acids mounted on biochips, researchers have discovered ribozymes, which are 100- or even 1000-fold more active catalytically. Fernandez et al. (2001) report data collected from a single molecule conformational change in a ribozyme. Fernandez et al. also report that such essentially duplex nucleic acid structures undergo "all or none" discrete transitions in conformation, not the progressive pair by pair binding one would expect.

A circular RNA that has enzymatic activity to cleave a separate RNA molecule at a cleavage site and RNA molecules capable of conferring stability to RNA in vivo through an endogenous ribozyme binding protein is described in U.S. Pat. No. 5,712,128 of Been et al. and U.S. Pat. No. 5,985,620 of Sioud.

Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridisation with complementary oligonucleotides, using ribonuclease protection assays.

Another way of providing inhibition is the use of engineered hammerhead motif ribozyme molecules that specifically and efficiently catalyse endonucleolytic cleavage of PlGF (or optionally VEGFR-1) RNA sequences for the treatment of Philadelphia chromosome positive leukemia in a subject, preferably a mammalian and yet more preferably a human. Anti-VEGFR-1-ribozyme, such as Angiozyme, which has been developed against VEGFR-1 mRNA by Ribozyme Pharmaceuticals Inc, Boulder, Colo. 80301, USA have already been used in cancer therapy (Weng and Usman, 2001; Pavco et al., 2000). This Angiozyme, among other anti-VEGFR-1 catalytic RNA molecules can be used for the inhibition of the PlGF receptor activity, which downregulate PlGF receptor function by specifically cleaving the mRNAs for the primary PlGF receptors, VEGFR-1. Clinical trials of an anti-VEGFR-1 ribozyme are currently in progress for breast cancer.

Other inhibitors envisaged herein are oligoribonucleotide sequences, that include anti-sense RNA and DNA molecules and siRNA constructs which are homologous to a part of the mRNA sequence of the PlGF gene or its receptor VEGFR-1 mRNA. RNA interference or "RNAi" is a term initially coined by Fire and co-workers to describe the observation that double-stranded RNA (dsRNA) can block gene expression (Fire et al., 1998). dsRNA directs gene-specific, post-transcriptional silencing in many organisms, including vertebrates, and has provided a new tool for studying gene function. RNAi involves mRNA degradation. PlGF can be silenced by a method of selective post-transcriptional silencing of the expression of PlGF in a cell of interest comprising introducing into said cell a siRNA construct which is homologous to a part of the mRNA sequence of said PIGF gene. Present invention provides a method for treating Ph+ leukemia in a subject by post-transcriptional gene silencing by RNA interference (RNAi) PIGF expression in cells and/or RNA interference (RNAi) VEGFR-1 expression in cells. This is a method of particular significance in vivo in a human patient. Likewise, the use of PIGF RNAi is envisaged for the treatment of Ph+ leukemia.

dsRNA used to initiate RNAi, may be isolated from native source or produced by known means, e. g. transcribed from DNA. For example, the binding of an RNA polymerase to a promoter (meaning any double-stranded sequence of DNA comprising a binding site recognised by a DNA-dependent RNA polymerase) permits initiation of transcription. Many known promoter sequences can be used to produce the dsRNA, for example, but not limited to, the sequences recognised by the RNA polymerases of phages T7, T3 or SP6. This does not, however, represent a limitation, because it will appear clearly to a person skilled in the art that any promoter sequence identified as such, and for which the corresponding RNA polymerase is available, can be used. Alternatively, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In fact, in accordance with U.S. Pat. No. 5,795,715, a DNA duplex provided at each end with a promoter sequence can directly generate RNAs of defined length, and which can join in pairs to form a dsRNA.

The dsRNA, whether of synthetic or natural origin, is subject to rapid degradation by nucleases present in the sera of various animal species, particularly primates. Consequently procedures involving dsRNA generally utilise baked glassware throughout, and all buffers are filtered, e. g. through a Nalgene 45 micron filter, for sterility. Pyrogen-free, double distilled water must be used for all solutions to minimise any possibility of endotoxin contamination.

The concentration of the dsRNA solution may be determined from its UV spectrum. For example, the molar concentration of natural or synthetic dsRNA is determined from the optical density (OD) at 260 nm using an extinction coefficient, obtainable from the literature or determined using standard procedures: 44.7 times OD260=micrograms dsRNA/ml.

If appropriate, the dsRNA solution can be diluted with pyrogen-free buffer for ease in handling. The resulting dsRNA can optionally be linked to a support; or to a ligand, such as biotin, which can be attached to a support coated with avidin. This permits direct quantification, when utilised as an analytical tool.

According to a particular embodiment, the dsRNA compositions of the present invention are prepared as pharmaceutical composition for the treatment of subjects, particularly for the treatment of human patients. More particularly the pharmaceutical compositions are administered to treat Philadelphia chromosome positive leukemia in human patients. In alternative embodiments, the compositions are used to create functional 'knockout' model organisms, those in which a target gene is defective, or in this case, expression is inhibited. The dsRNA pharmaceutical composition can be administered locoregionally to said patient. The dsRNA pharmaceutical compositions of the present invention preferably contain a pharmaceutically acceptable carrier or excipient suitable for rendering the compound or mixture administrable e.g. parenterally, intravenously, intradermally, intramuscularly or subcutaneously, or transdermally. The active ingredients may be admixed or compounded with any conventional, pharmaceutically acceptable carrier or excipient.

Selected siRNAs for silencing VEGFR1 gene with high probability of functionality and knocking down more than 90% of the mRNA are available from Dharmacon Inc. Lafayette, Colo. 80026, USA. A pooling of several different siRNA duplexes all directed against one target gene, called SMARTpooling/SMARTselection is used as an efficient technology for silencing the VEGFR1 gene and/or the PIGF gene. siRNAs against PIGF are also commercially available (e.g. Santa Cruz Biotechnology Inc.).

Anti-sense RNA and DNA molecules act to directly block the translation of mRNA by binding to targeted mRNA and preventing protein translation. In regard to antisense DNA, oligodeoxyribonucleotides derived from the translation initiation site, e.g. between −10 and +10 regions of the VEGFR-1 or PIGF nucleotide sequence, are particularly envisaged. For instance the downregulation of another tyrosine kinase receptor, VEGFR2 receptor, achieved by VEGFR2 antisense oligonucleotide transfection, has already been achieved by standard antisense technology (Berard et al., 1997). Moreover antisense (AS) oligonucleotides directed against the PIGF receptor VEGFR1 has been demonstrated in vivo to block angiogenesis (Marchand et al., 2002). Moreover, antisense inhibition of PIGF protein production has already been demonstrated by Yonekura et al. (1999).

Both anti-sense RNA and DNA molecules as well as ribozymes may be prepared by any method known in the art for the synthesis of RNA (or DNA) molecules. These include techniques for chemically synthesising oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesise anti-sense RNA constitutively or inducibly, depending on the promoter used, can be introduced stably into cell lines.

In a specific embodiment it should be clear that the therapeutic method of the present invention for the treatment of Philadelphia chromosome positive leukemia can also be used in combination with any other therapy known in the art for the treatment of Ph+ leukemia. Particularly envisaged therapies include protein tyrosine kinase inhibitors, particularly BCR/ABL inhibitors, e.g. imatinib and the like.

The term 'medicament' as used in the application relates to a composition comprising molecules (inhibitors) as described above and a pharmaceutical acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The 'medicament' may be administered by any suitable method within the knowledge of the skilled man. The preferred route of administration is parenterally.

In parenteral administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the PlGF inhibitor (e.g. protein, polypeptide, peptide, nucleic acid, compound or molecule) is given at a dose between 1 µg/kg and 10 mg/kg, more particularly between 10 µg/kg and 5 mg/kg, most particularly between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more particularly between 7 and 15 µg/kg/minute.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutical active substances is well known in the art. Except insofar as any conventional media or agent is incompatible with the compositions of this invention, its use in the therapeutic formulation is contemplated. Supplementary active ingredients can also be incorporated into the pharmaceutical formulations.

It will be understood by those skilled in the art that any mode of administration, vehicle or carrier conventionally employed and which is inert with respect to the active agent may be utilised for preparing and administering the pharmaceutical compositions of the present invention. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g. the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and particularly from about 0.1 to about 100 mg/kg. A 'therapeutic amount' or therapeutically effective amount as used herein is an amount that ameliorates one or more symptoms of a disease. Such amount will typically depend on the inhibitor and the severity of the disease, but can be decided by the skilled person, possibly through routine experimentation.

Another aspect of administration for treatment is the use of gene therapy to deliver the above mentioned anti-sense gene or functional parts of the PlGF gene or a ribozyme directed against the PlGF mRNA or a functional part thereof. Gene therapy means the treatment by the delivery of therapeutic nucleic acids to patient's cells. This is extensively reviewed in Lever and Goodfellow 1995; Br. Med Bull., 51, 1-242; Culver et al., 1995; Ledley, 1995. To achieve gene therapy there must be a method of delivering genes to the patient's cells and additional methods to ensure the effective production of any therapeutic genes.

Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid—or DNA-binding agent has been attached for the specific targeting of nucleic acids to cells (Cristiano et al., 1993). Target cells will typically depend on which symptoms need to be treated and can be selected by the skilled person (e.g. bone marrow cells or stromal cells to treat leukemia).

The gene therapy vectors should express a therapeutic amount of the PlGF inhibitor. According to particular embodiments, the gene therapy vectors described in this application direct the expression of a therapeutic amount of the gene product for an extended period. Indeed, as long as therapeutic levels are achieved, no new treatment is necessary. Typically, therapeutic expression is envisaged to last at least 20 days, at least 50 days, at least 100 days, at least 200 days, and in some instances 300 days or more. Expression of the gene product (e.g. polypeptide, RNAi, etc.) encoded by the coding sequence can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Gene therapy vectors can be episomal vectors (i.e., that do not integrate into the genome of a host cell), or can be vectors that integrate into the host cell genome. Examples of episomal vectors include (extrachromosomal) plasmids and so-called mini-circles, which are composed of the expression cassette only and are devoid of bacterial sequences, and examples of vectors that integrate into the host cell genome including viral vectors.

Representative plasmid vectors include pUC vectors, bluescript vectors (pBS) and pBR322 or derivatives thereof that are devoid of bacterial sequences (minicircles). Some of the plasmid vectors can be adapted to incorporate elements that enhance episomal plasmid persistence in the transfected cells. Such sequences include S/MARs that correspond to scaffold/matrix attached region modules linked to a transcription unit (Jenke et al., 2004; Manzini et al., 2006).

Representative viral vectors include vectors derived from adeno-associated virus, adenovirus, retroviruses and lentiviruses. Alternatively, gene delivery systems can be used to combine viral and non-viral components, such as nanoparticles or virosomes (Yamada et al., 2003).

Retroviruses and lentiviruses are RNA viruses that have the ability to insert their genes into host cell chromosomes after infection. Retroviral and lentiviral vectors have been developed that lack the genes encoding viral proteins, but retain the ability to infect cells and insert their genes into the chromosomes of the target cell (Miller, 1990; Naldini et al., 1996). The difference between a lentiviral and a classical Moloney-murine leukemia-virus (MLV) based retroviral vector is that lentiviral vectors can transduce both dividing and non-dividing cells whereas MLV-based retroviral vectors can only transduce dividing cells.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and nondividing cells in many different tissues in vivo including airway epithelial cells, endothelial cells, hepatocytes and various tumors (Trapnell, 1993).

Adeno-associated virus (AAV) is a small ssDNA virus which infects humans and some other primate species, not known to cause disease and consequently causing only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited.

Another viral vector is derived from the herpes simplex virus, a large, double-stranded DNA virus. Recombinant forms of the vaccinia virus, another dsDNA virus, can accommodate large inserts and are generated by homologous recombination.

The inhibitors listed herein can be used for the treatment of Philadelphia chromosome positive (Ph+ or BCR-ABL+) leukemia, or be used for the manufacture of a medicament for the treatment of Ph+ (BCR-ABL+) leukemia. Methods for the treatment of Ph+/BCR-ABL+ leukemia will typically involve administration of such PlGF inhibitor to a subject in need thereof, most particularly a human subject. A particular subset of Ph+ leukemias are the chronic myelogenous leukemias (CMLs). Thus, according to particular embodiments, the uses and methods described in the application are for the treatment of CML. Another important category of Ph+ leukemias is a group of acute lymphocytic leukemias (ALLs) also characterized by the presence of the Philadelphia chromosome. This category typically has a bad prognosis, as many standard treatments fail in Ph+ ALL cases. According to a particular embodiment, the other leukemias wherein the Philadelphia chromosome (or the BCR-ABL fusion protein) is present may also be suitable for the uses and methods described herein. However, these cases are less common than CML or ALL. Nevertheless, some cases of Ph+ AML (acute myeloid leukemia) have been reported, and such cases of Ph+ leukemia are also envisaged to benefit from the uses and methods provided in the application.

It is important to realize that leukemias are devastating diseases, often with a bad prognosis for the patient. Therefore, it is important to be able to offer alternative treatment strategies, or combination strategies, if one approach of treatment fails. It is a goal of the present application to provide therapeutic benefit, in particular also to patients that do not benefit from other treatment regimen.

The standard treatment for Philadelphia chromosome positive leukemias, in particular for CML, is the use of a BCR-ABL inhibitor or a tyrosine kinase inhibitor. The best known example of this type of drugs is imatinib, but several other examples exist, such as nilotinib (AMN107), dasatinib (BMS354825), AT9283 (Astex therapeutics), SGX393 (Eli Lilly), INNo-406 (Innovive Pharmaceuticals), bosutinib (SKI606), and MK0457 (Merck).

However, several reports indicate that resistance against these medicines is a common problem. Indeed, leukemia cells persist even in successfully treated patients, and some patients develop resistance and ultimately relapse (Swords et al., 2007; Buchert, 2007; Li and Li, 2007; Kujawski and Talpaz, 2007). According to particular embodiments, the PlGF inhibitors are used for the treatment of Ph+ leukemias which can not be treated with a BCR-ABL inhibitor, and/or in more particular cases can not be treated with a BCR-ABL inhibitor alone. Philadelphia chromosome positive leukemias may not be treatable with a BCR-ABL inhibitor (or a BCR-ABL inhibitor alone) for a variety of reasons, the two most common being insensitivity of the malignant cells to the BCR-ABL inhibitor and the medicine not being tolerated by the patient.

Insensitivity of the leukemia cells to the BCR-ABL inhibitor may be due to several mechanisms (Shah and Sawyers, 2003), and may arise from onset (i.e. insensitivity at the first treatment) or the resistance may be acquired (e.g. in patients showing relapse, or in patients having a further developed leukemia, for instance in a blast crisis stage).

Also, BCR-ABL inhibitors have been known to invoke adverse side-effects in patients, which may lead to the medicament not being suitable anymore for particular patients. An allergic reaction in a patient may also lead to intolerance to the medicine.

According to specific embodiments, the PlGF inhibitors are used for the treatment of Ph+ leukemias which are (at least partially) resistant to treatment with a BCR-ABL inhibitor. Leukemias which are (partially) resistant to a BCR-ABL inhibitor can be defined as leukemias in which leukemic cells are present that have a diminished response to the BCR-ABL inhibitor. The amount of cells having a diminished response is indicative of the degree of resistance to the BCR-ABL inhibitor. Typically, although not necessarily, (partial) resistance to a BCR-ABL inhibitor is an acquired phenomenon. According to further specific embodiments, the PlGF inhibitors are used for the treatment of imatinib-resistant Ph+ leukemias. Non-limiting examples of such leukemias include imatinib-resistant Ph+ CML, imatinib-resistant Ph+ ALL, e.g. imatinib-resistant Ph+ T-ALL, imatinib-resistant Ph+ B-ALL.

Sometimes, although certainly not in all cases, the resistance to BCR-ABL inhibitors, in particular resistance to imatinib, is associated with mutations in the BCR-ABL gene, in particular in the tyrosine kinase domain. The T315I mutation is the best known example hereof. Other examples include the E255K, E255V, Y253H, H396P, F317L, M351T, G250E, F311L, M244V, F359V, L387M, H396R, Q252H, Y253F, Q252R, and E355G mutations (Shah and Sawyers, 2003). Corbin et al. reported that especially G250E, H396P, H396R, E255V and T315I appeared to confer resistance to imatinib (Corbin et al., 2003). According to particular embodiments, the PlGF inhibitors are used for the treatment of Ph+ leukemias in which the BCR-ABL gene has at least one mutation. According to further particular embodiments, the PlGF inhibitors are used for the treatment of Ph+ leukemias which can not be treated with a BCR-ABL inhibitor and/or not be treated with a BCR-ABL inhibitor alone, and in which the BCR-ABL gene has at least one mutation. According to still further particular embodiments, the Ph+ leukemias can not be treated with imatinib or not be treated with imatinib alone. According to still more specific embodiments, the at least one mutation in the BCR-ABL gene is selected from the group consisting of the T315I, E255K, E255V, Y253H, H396P, F317L, M351T, G250E, F311L, M244V, F359V, L387M, H396R, Q252H, Y253F, Q252R, and E355G mutations.

It is envisaged that the use of an inhibitor of placental growth factor for the treatment of Philadelphia chromosome positive leukemia can be a stand-alone therapy or method of treatment. According to particular embodiments, however, the use of PlGF inhibitors in the treatment of Ph+ leukemias is envisaged as part of a combination therapy. Thus, PlGF inhibition may be used together with other therapies used to treat Ph+ leukemias, such as radiotherapy, chemotherapy, biological therapy (e.g. interferon treatment), stem cell transplantation, bone marrow transplantation, surgery (e.g. spleen removal), or targeted therapies such as BCR-ABL inhibition, Lyn inhibition, Hsp90 inhibition, Src inhibition. Of course, PlGF inhibition may be used in combination with more than one of these therapies (e.g. together with BCR-ABL and Lyn inhibition).

PlGF inhibition may be done concomitant with other therapies, or either before or after other therapies, or they may e.g. be intermittently changed. The skilled person is able to decide on the optimal treatment regimen, optionally after routine experimentation.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Materials and Methods
Animals

Female Balb/c mice (8 weeks old) were obtained from Janvier. Housing and all experimental animal procedures were approved by the Institutional Animal Care and Research Advisory Committee of the K.U. Leuven.

Cells and Culture Conditions

KCL-22 and CRL-1929 cells were obtained from ATCC. Bv-173, K562, BaF3, 32D and Nalm6 cells were kindly provided by J. Cools (VIB, Leuven). Bv-173 cells and K562 cells were cultured in RPMI medium (Gibco, Invitrogen Corporation) with 20% FCS (Hyclone Laboratories); BaF3, 32D and KCL-22 cells were cultured in RPMI medium with 10% FCS; Nalm 6 cells were cultured in DMEM medium (Gibco, Invitrogen Corporation) with 10% FCS and CRL-1929 cells were cultured in IMDM medium (Gibco, Invitrogen Corporation) with 20% FCS and 0.05 mM beta-mercaptoethanol (Gibco, Invitrogen Corporation).

Isolation of Primary Murine Bone Marrow-derived Stromal Cells (BMDSCs)

For isolation of BMDSCs, the bone marrow from femurs and tibias was flushed, the erythrocytes eliminated with lysis buffer (150 mM NH4Cl, 0.1 mM EDTA, 10 mM KHCO3, pH 7.4) and subsequently the cells were cultured in DMEM medium supplemented with 15% FCS. After 24 hours, the non-adherent cell fraction was removed, and the adherent cells were further cultured and expanded for 3 weeks.

Proliferation Assays and Co-cultures

Proliferation of leukemia cells and BMDSCs was analyzed by using MTT assays or by manual counting with a hemocytometer. Murine recombinant PlGF and anti-VEGFR-1 were obtained from R&D Systems. Anti-PlGF and control IgG1 were produced by Thrombogenics and BioInvent and characterized as described (Fischer et al., 2007). PlGF was used at a concentration of 50 ng/ml and the antibodies in 100-fold molar excess, unless stated otherwise. For co-culture experiments, $10^5$ BMDSCs were co-cultured for 48 hours with $4 \times 10^5$ leukemia cells alone or in presence of the respective antibodies in serum-free medium. Subsequently, numbers of adherent BMDSCs and non-adherent leukemia cells were determined and supernatants were harvested for analyses of PlGF and VEGF protein.

Peripheral Blood Analysis

Blood was collected with capillary pipettes by retro-orbital bleeding, and white blood cell count (WBC) determined using an automated cell counter (Beckman Coulter).

ELISA

Concentrations of PlGF or VEGF were quantified in cell culture supernatants, peripheral blood plasma and bone marrow plasma using "Quantikine" mouse PlGF and mouse VEGF immunoassays (R&D Systems). Concentrations were expressed as pg/ml/$10^5$ cells or as pg/ml.

Quantitative Real-time PCR

RT-PCR was essentially carried out with primers and probes as described previously (Fischer et al., 2007).

Syngeneic Model of BCR-ABL+ Pre-B Cell Leukemia

BCR-ABL+ BaF3 cells were cultured as described above and $1 \times 10^6$ cells were injected via the tail vein into syngeneic 8 weeks old Balb/C mice.

Transplantation Models of Imatinib-sensitive and Imatinib-resistant CML

For induction of CML, bone marrow cells were harvested by flushing of femurs and tibias from Balb/C donors (8 weeks) 4 days after treatment with 200 mg/kg 5-fluorouracil (5-FU; Sigma Aldrich) and pre-stimulated in vitro in medium containing 10 ng/ml IL-3, 10 ng/ml IL-6 and 50 ng/ml SCF. Subsequently, the cells were subjected to 1 round of co-sedimentation with retroviral stocks (retroviral constructs: MCSV-GFP, MSCV-BCR-ABL p210 IRES-EGFP, MSCV-BCR-ABL-T315I-IRES-EGFP; kindly provided by Jan Cools). Recipient female mice were prepared by lethal irradiation, and transduced marrow was transplanted by intravenous injection of 0.5×106 cells per animal.

Example 1

Analysis of PlGF Expression in Leukemia Cells and Primary Bone Marrow Stromal Cells in Vitro In order to determine the expression profile of PlGF by leukemia cells and by different populations of leukemia-associated stromal cells in vitro, PlGF expression was analyzed in a set of BCR-ABL+ myeloid and lymphoid cell lines (murine: BaF3, 32D; human: K562, Bv-173, KCL-22). In addition, the human BCR-ABL-lymphoid cell line Nalm-6 was investigated. Furthermore, PlGF expression was quantified in different populations of bone marrow stromal cells. No expression of PlGF protein was found in all studied leukemia cell lines as determined by ELISA and very low amounts (41±2.3 pg/ml) in healthy CD45$^+$ hematopoietic cells isolated from murine bone marrow (FIG. 1A). In contrast, murine primary bone marrow-derived stromal cells (BMDSCs) and stromal cell lines (S17, OP9) expressed abundant amounts of PlGF protein (FIG. 1A).

FACS analysis of bone marrow-derived stromal cells revealed that 49.7%±20% of murine BMDSCs were of hematopoietic lineage after a mean culture period of 3 weeks (not shown). To unravel, whether the hematopoietic fraction (CD45+) or the non-hematopoietic fraction (CD45−) of murine BMDSCs expressed PlGF, we separated both populations via an immunomagnetic approach (purity>93%, not shown) and subsequently determined PlGF in the supernatants of CD45+ and CD45− BMDSCs. These experiments revealed almost exclusive expression of PlGF by CD45− BMDSCs (FIG. 1B) (N=3; p<0,001). Furthermore, we determined PlGF expression in human (HUVEC) and murine (fEND5) endothelial cells and found abundant expression of PlGF protein (HUVEC: 279.7±29.9 pg/ml; fEND5: 125.7±18.8 pg /ml; N=3) Altogether, these results point into the direction that PlGF is mainly expressed by bone marrow stromal cells and not by leukemia cells in vitro.

Example 2

Figure 2:
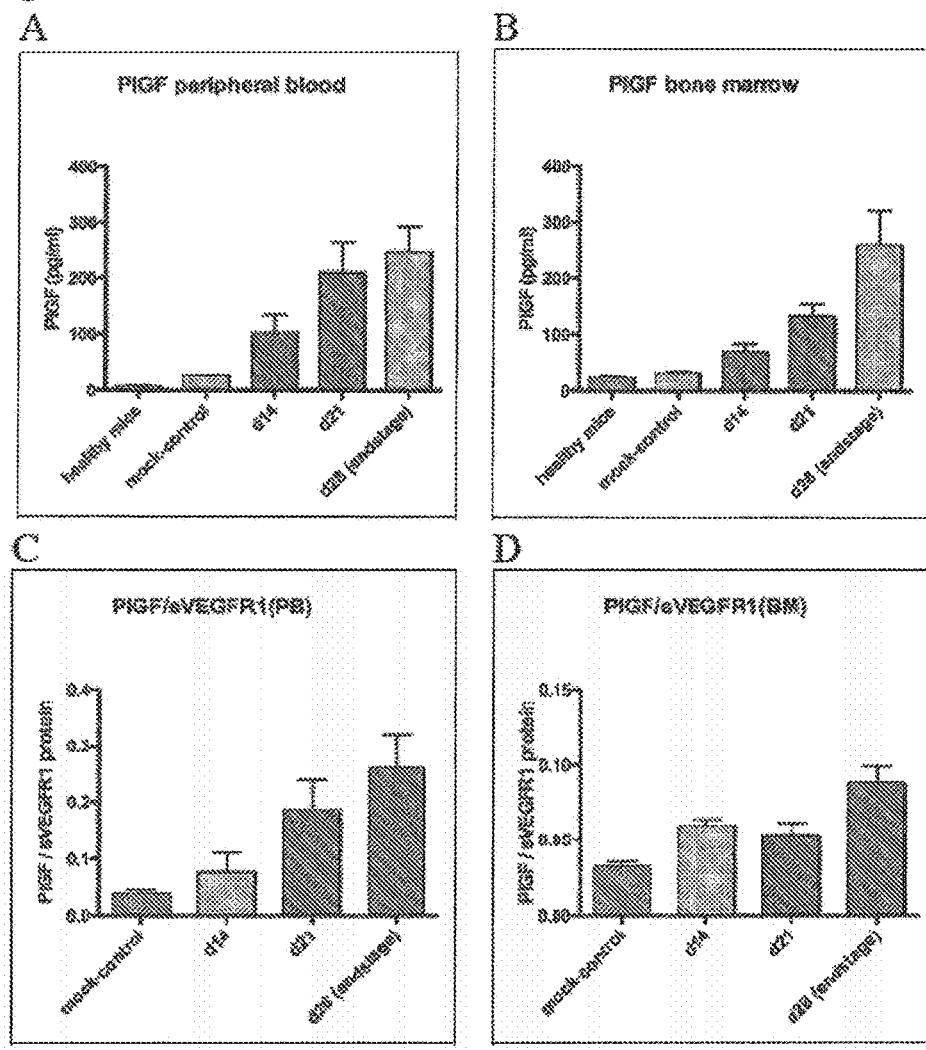
In FIG. 2, expression of PlGF and other molecules is shown in vivo (for details, see Example 2). A, B: PlGF protein levels in peripheral blood or bone marrow at different timepoints of leukemic disease progression in mice; C, D: Ratio of PlGF vs. sVEGFR-1 protein levels in peripheral blood or bone marrow at different timepoints of leukemic disease progression in mice; E: bone marrow PlGF mRNA expression in healthy and leukemic mice, * indicates p<0.002; F: characterization of PlGF expression in subpopulations of bone marrow, * indicates p<0.05; G: bone marrow VEGF mRNA expression in healthy and leukemic mice; H, I: PlGF protein levels in peripheral blood or bone marrow correlate with leukemic burden in end-staged diseased mice.
Figure 2:
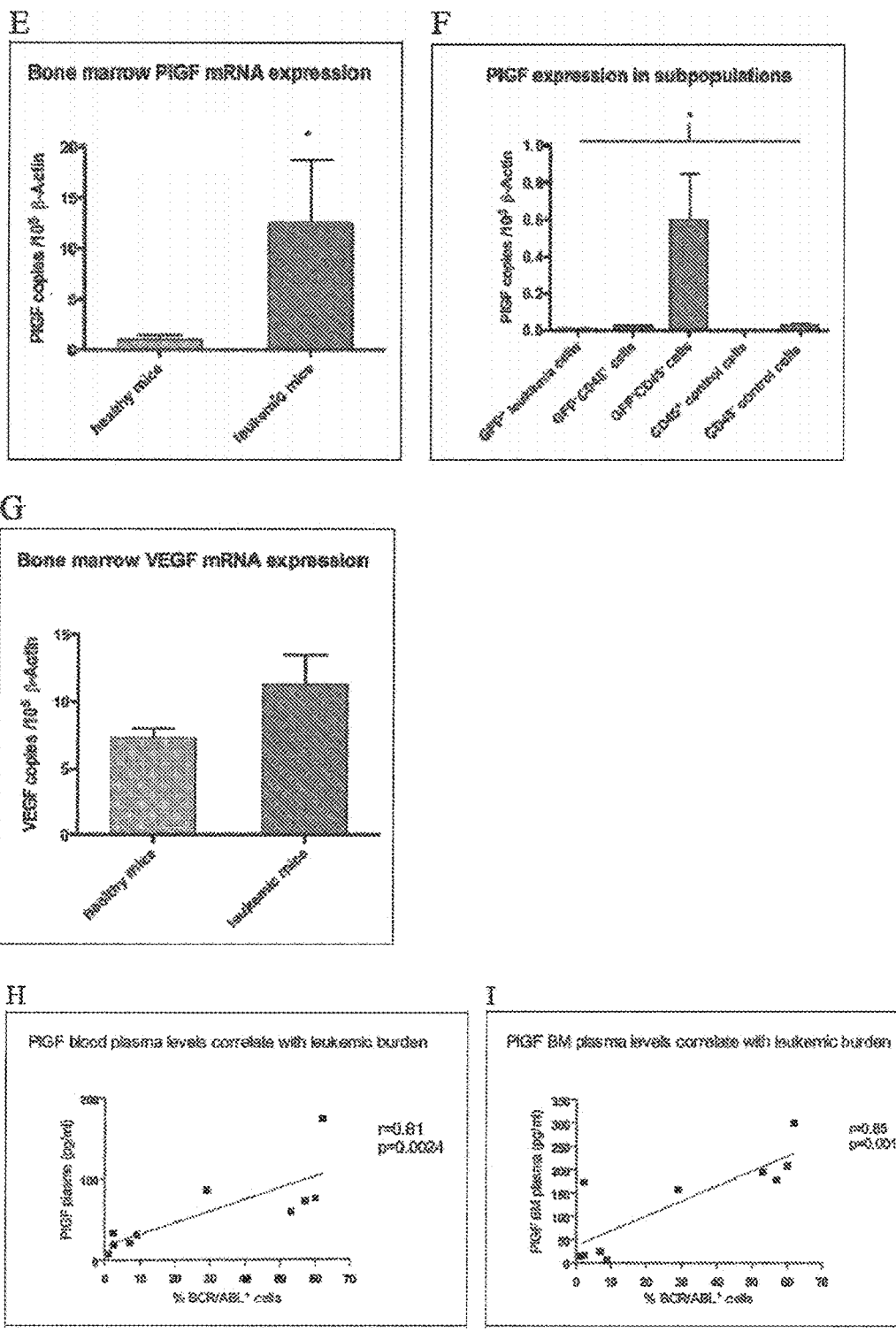

PlGF is Expressed by the Leukemic Stroma and Represents a Biomarker of Leukemia Progression in Vivo To elucidate a potential impact of PlGF on leukemia disease progression and hence therapeutic potential of αPlGF in vivo, a well-described blast crisis model of CML was used by transplanting BCR/ABL-GFP transduced bone marrow into syngeneic, sublethally irradiated mice. We first analyzed PlGF protein levels in the plasma of diseased mice at different timepoints (d14, d21 and d28) compared to control mice, and detected very low amounts of PlGF protein in the peripheral blood of healthy mice or mice transplanted with mock-transduced bone marrow and low amounts of PlGF protein in their bone marrow. In contrast, leukemic mice showed increasing PlGF protein upon disease progression in their circulation reaching levels comparable to mice bearing solid tumors (Fischer et al., 2007) at end-stage (FIGS. 2A, B). A similar kinetic of PlGF increase was observed in bone marrow plasma (FIG. 2B). We also quantified the natural inhibitor of PlGF, sVEGFR-1, and found that although sVEGFR-1 is present in excess compared to PlGF, the ratio PlGF/sVEGFR-1 increases in blood and bone marrow upon disease progression, indicating that upregulation of PlGF is more pronounced than of sVEGFR-1 during the course of leukemia (FIGS. 2C, D).

To dissect the source of PlGF in vivo, we performed Real-Time PCR analyses of bone and bone marrow, revealing 12.6-fold upregulation of PlGF mRNA in the bone marrow (N=8 ; P<0.002) (FIG. 2E). PlGF mRNA levels in the bones were similar in diseased and healthy mice (data not shown), indicating that the primary source of elevated PlGF detected in the bone marrow plasma of leukemic mice is the bone marrow. To further specify the PlGF producing cells within the bone marrow, we FACS-sorted leukemia cells (GFP+), non-leukemic hematopoietic cells (GFP− CD45+) and non-leukemic, non-hematopoietic stromal cells (GFP−CD45−) and subsequently determined PlGF mRNA expression by means of RT-PCR in these subfractions. These experiments elucidated, similar to the above-mentioned in vitro findings, that PlGF is predominantly expressed by CD45− stromal cells and only negligibly by leukemia cells or hematopoietic cells in leukemic mice in vivo. Indeed, GFP−CD45− stromal cells expressed 95, 6-fold more PlGF mRNA than leukemia cells and 32-fold more PlGF mRNA than hematopoietic cells (N=4; P<0.05); FIG. 2F). When comparing PlGF mRNA levels in CD45− bone marrow cells from leukemic mice with PlGF mRNA levels in CD45− cells from the bone marrow of healthy mice, we found a strong (25, 4-fold) upregulation of PlGF expression within the non-hematopoietic stromal cell compartment of mice bearing leukemia (N=4; P<0.05) (FIG. 2F). Interestingly, VEGF mRNA was only slightly upregulated in the bone marrow of mice bearing leukemia when compared to healthy mice (N=8; P=0.23) (FIG. 2G) indicating that PlGF represents a specific, stroma-derived pathogenic factor in BCR/ABL+ leukemia also in vivo. This hypothesis is further corroborated by the observation, that the amount of PlGF protein present in the blood plasma or bone marrow plasma of leukemic mice correlates with the number of leukemic blasts infiltrating the bone marrow, as determined by FACS analysis of GFP+ cells in the bone marrow of end-stage diseased mice (r=0.81 and r=0.85; p<0.05 ; FIGS. 2H, I). Hence, PlGF represents a biomarker of disease progression of blast crisis CML in mice.

Example 3

Anti-PlGF Inhibits PlGF-Induced Proliferation of Leukemia Cells

Figure 3:
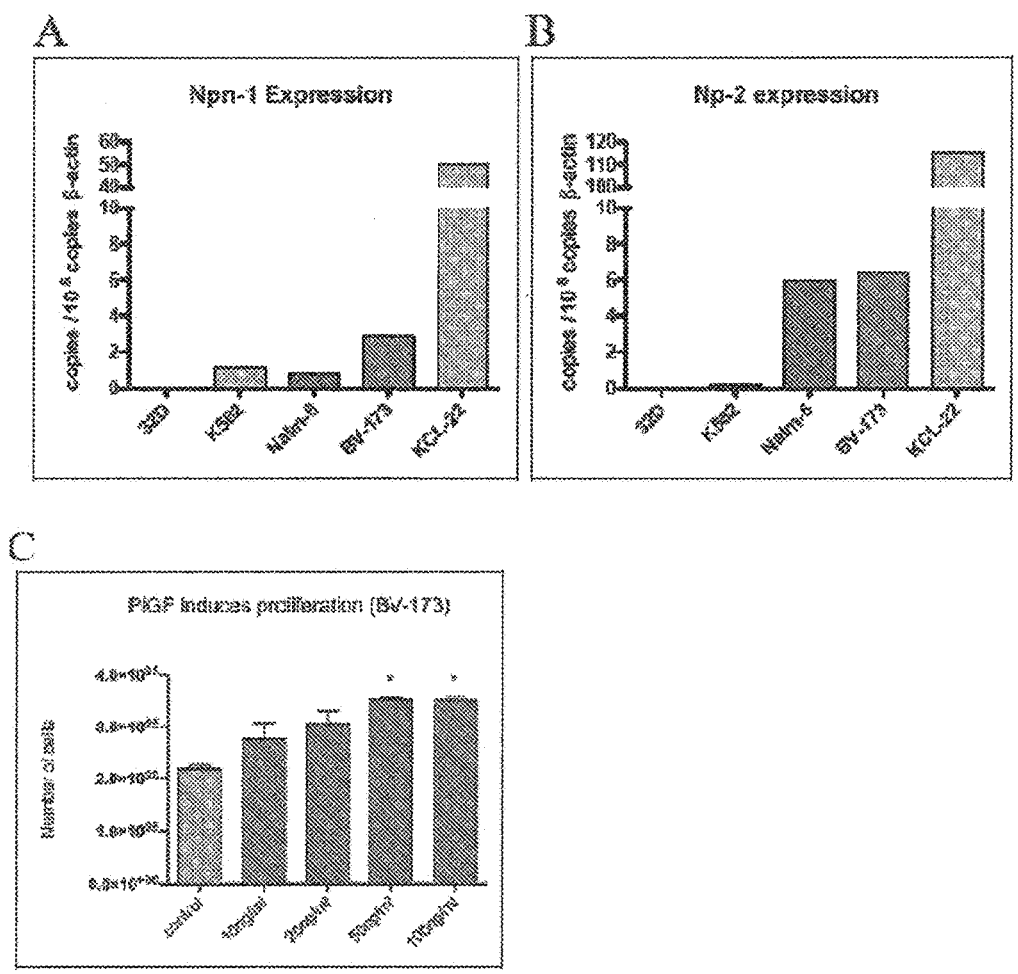
FIG. 3 demonstrates proliferation of leukemia cells by PlGF (for details, see Example 3). A, B: expression of Npn-1 and Npn-2 in different leukemia cell lines; C: induction of proliferation in the BV-173 cell line by different concentrations of PlGF; D: induction of proliferation by 50 ng/ml PlGF in a K562 (upper left panel), BV-173 (upper right panel), KCL-22 (lower left panel) and BaF3 (lower right panel) cell line, respectively; E: inhibition of PlGF induced proliferation in the BV-173 cell line by an anti-VEGFR-1 antibody; F: inhibition of PlGF induced proliferation in the BV-173 cell line by an anti-PlGF antibody. BM: bone marrow; PlGF: placental growth factor; αVEGFR-1: anti-vascular endothelial growth factor receptor-1 antibody; αPlGF: anti-PlGF antibody.
Figure 3:
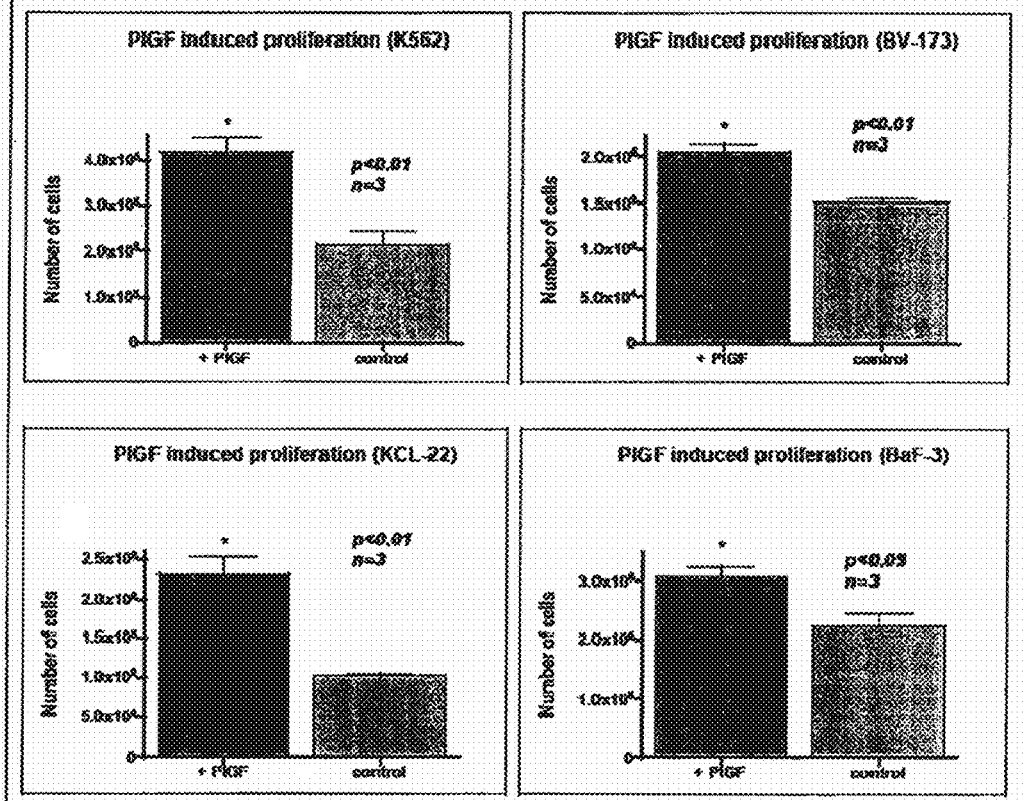
Figure 3:
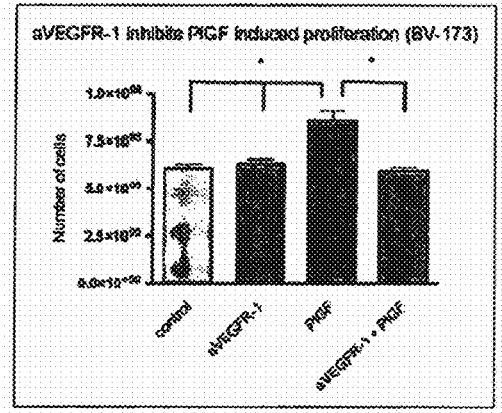
Figure 3:
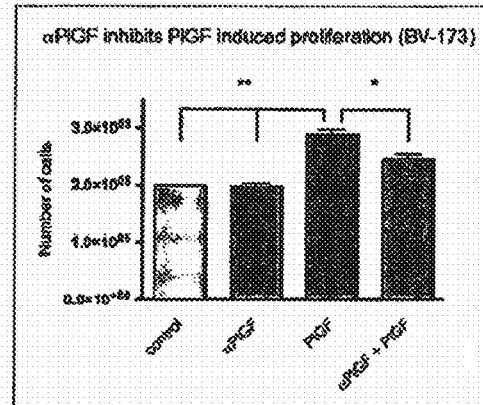

To determine a potential biological effect of PlGF on leukemia cells, expression of the main PlGF receptor, VEGFR-1 and its co-receptors Npn1 and Npn2 in leukemia cell lines was investigated. VEGFR-1 was expressed by most studied cell lines in accordance with the published literature (Fragoso et al., 2006) (data not shown). Npn1 and Npn2 were expressed in K562, Nalm-6, BV-173 and KCL-22 cell lines, albeit at different levels, but not in 32D cells (FIGS. 3A, B). Based on these findings, we incubated leukemia cells with PlGF in vitro, which dose dependently induced proliferation of 4 out of 5 BCR/ABL+ cell lines, in concordance with the published literature (FIGS. 3C, D). In addition to its main receptor VEGFR-1, PlGF also binds to the co-receptors Npn-1 and Npn-2. To unravel whether PlGF-induced proliferation of leukemia cells requires VEGFR-1, the inhibitory effect of an extracellular VEGFR-1 blocking antibody (αVEGFR-1) was evaluated. Inhibition of PlGF mediated proliferation in presence of αVEGFR-1 was found (FIG. 3E). In contrast, PlGF-induced proliferation of leukemia cells was not inhibited upon addition of extracellular, function blocking antibodies against Npn-1 and Npn-2, indicating that the pro-proliferative effect of PlGF is primarily mediated via VEGFR-1. (FIG. 1G). In a next step, it was investigated if anti-PlGF (αPlGF) inhibits PlGF induced proliferation of leukemia cells and nearly complete abrogation of the pro-proliferative effect of PlGF upon addition of αPlGF was found, indicating therapeutic potential in leukemia (FIG. 3F).

In order to elucidate, whether PlGF induces changes in ABL phosphorylation of BCR/ABL+ leukemia cells, we performed Western Blots of Bv-173 and KCL-22 cells that were incubated with and without PlGF. These experiments indicated that PlGF did not modify phosphorylation of ABL (data not shown).

Example 4

Figure 4:
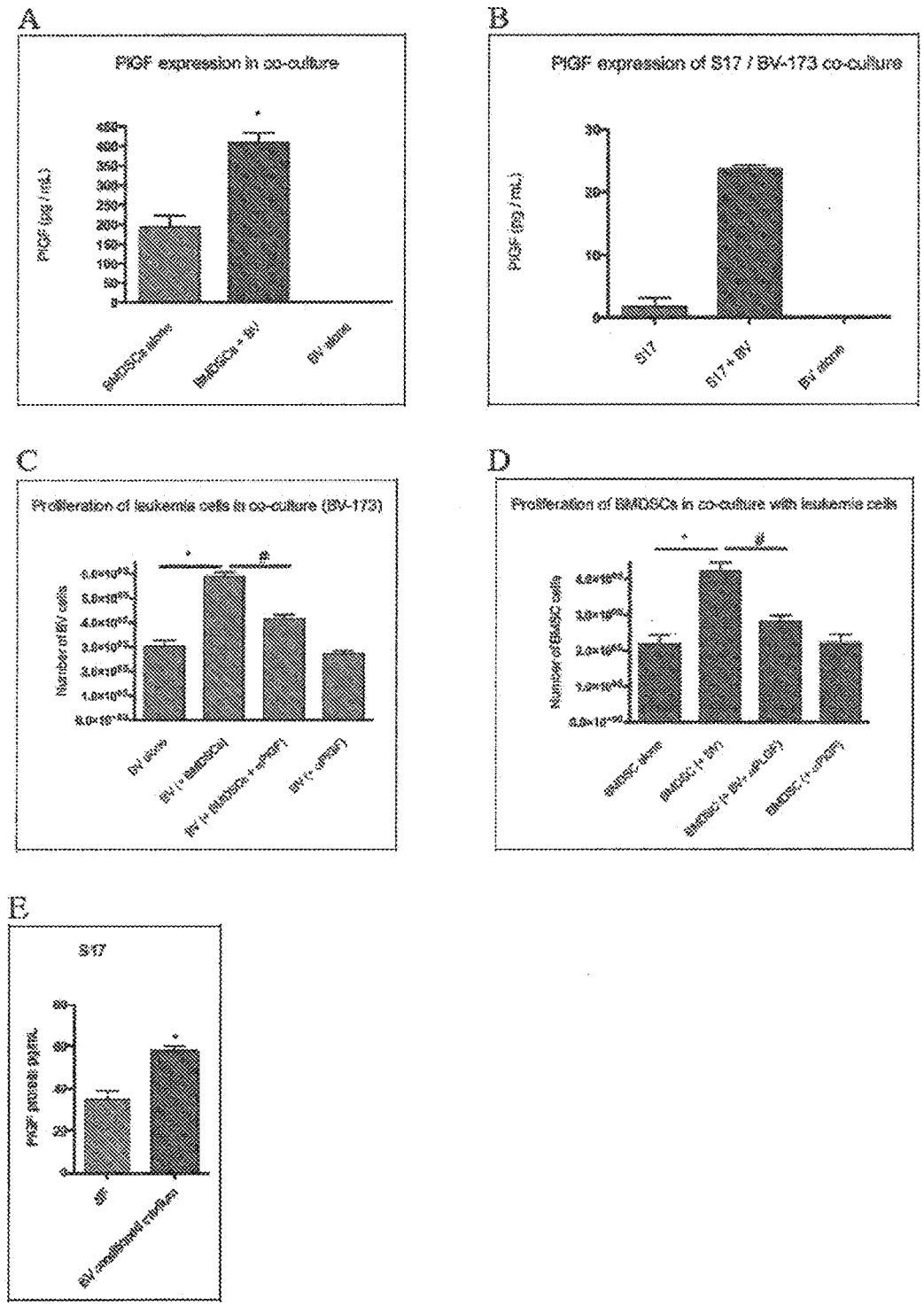
In FIG. 4, induction by paracrine interaction between leukemia cells and BMDSCs in vitro is shown (A-D), as well as with leukemia-cell conditioned medium (E). A: PlGF expression in BDMSCs, in the BV-173 cell line and in co-culture (BMDSCs+BV); B: PlGF expression in S17 cells, in the BV-173 cell line and in co-culture; C: proliferation of BV-173 leukemia cells alone and in co-culture with BMDSCs, and inhibition by an anti-PlGF antibody; D: proliferation of BMDSCs alone and in co-culture with BV-173 leukemia cells, and inhibition by an anti-PlGF antibody; E: PlGF upregulation in S17 cells by incubation with a leukemia cell (BV-173) conditioned medium. BV: BV-173 cell line; αPlGF: anti-PlGF antibody.

Paracrine Interactions Between Leukemia Cells and BMDSCs Induce PlGF Secretion by BMDSCs Co-culture experiments were performed to study potential interactions between human leukemia cells and murine BMDSCs or a murine bone marrow stromal cell line (S17) leading to increased PlGF secretion by either BMDSCs or S17 cells and significant upregulation of murine PlGF upon co-culture was found (FIGS. 4A,B). This finding prompted us to analyze proliferation of the co-cultures, which revealed significant induction of proliferation of leukemia cells and BMDSCs (FIGS. 4C, D). This pro-proliferative effect was almost entirely abrogated upon addition of αPIGF to the cultures, indicating that PIGF can induce proliferation of leukemia cells in a paracrine manner, but at the same time mediates expansion of bone marrow stromal cells via an autocrine loop, thus simultaneously promoting the leukemic clone and its supportive stroma (FIGS. 4C, D). Interestingly, this interaction specifically leads to PIGF upregulation, because VEGF was not upregulated upon co-culture (data not shown). To test the potential role of PIGF in BCR-ABL+ leukemia in vivo, 3 different murine models of BCR/ABL+ myeloid and lymphoid leukemia were established.

In an effort to unravel molecular signals that might induce upregulation of PIGF, we first analyzed, whether incubation with leukemia-cell conditioned medium (CM) would be sufficient to induce similar upregulation of PIGF in stromal cells (S17) than direct co-culture with leukemia cells, and found that indeed CM is sufficient for induction of PIGF secretion by S17 (N=3; P=0.008; FIG. 4E).

Example 5

Figure 5:
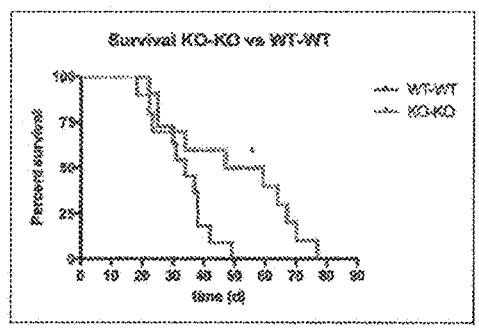
FIG. 5A: survival of leukemic PlGF$^{-/-}$ and WT mice; B: survival of cross-over leukemic mice (for details, see Example 5); C: survival of mice bearing leukemia induced by lymphatic BCR-ABL+ BaF3 cells, either treated with an anti-PlGF antibody or a control antibody; D, E: FACS analysis of BCR-ABL+ cells at early stage (d15) and end-stage (d28) leukemia and effect of inhibition with anti-PlGF antibody; F: bone marrow histology of control and anti-PlGF treated end-stage leukemic mice; G: Survival in a mouse model of imatinib-sensitive CML, either treated with an anti-PlGF antibody or a control antibody; H: Survival in a mouse model of imatinib-resistant CML, either treated with an anti-PlGF antibody or a control antibody. αPlGF: anti-PlGF antibody; d: days; T315I: the T315I mutation of the BCR-ABL fusion protein. For more details, see Example 6.
Figure 5:
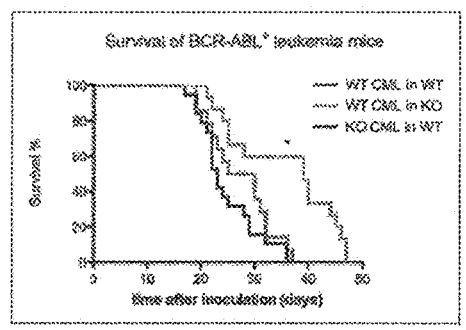
Figure 5:
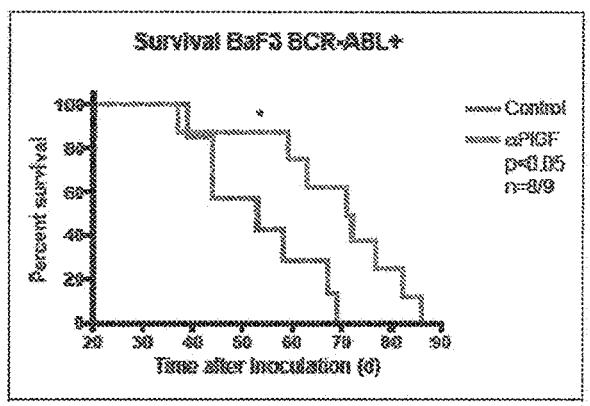
Figure 5:
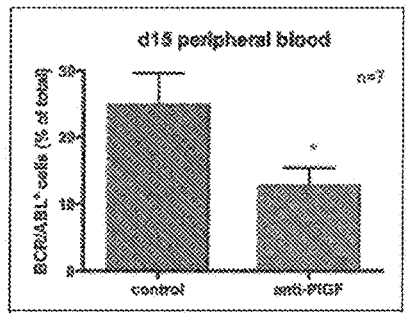
Figure 5:
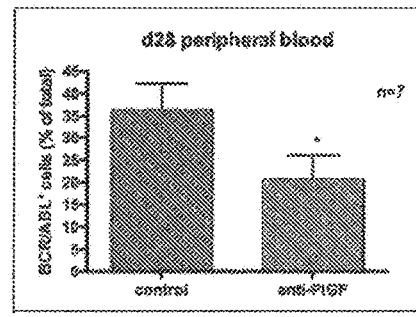
Figure 5:
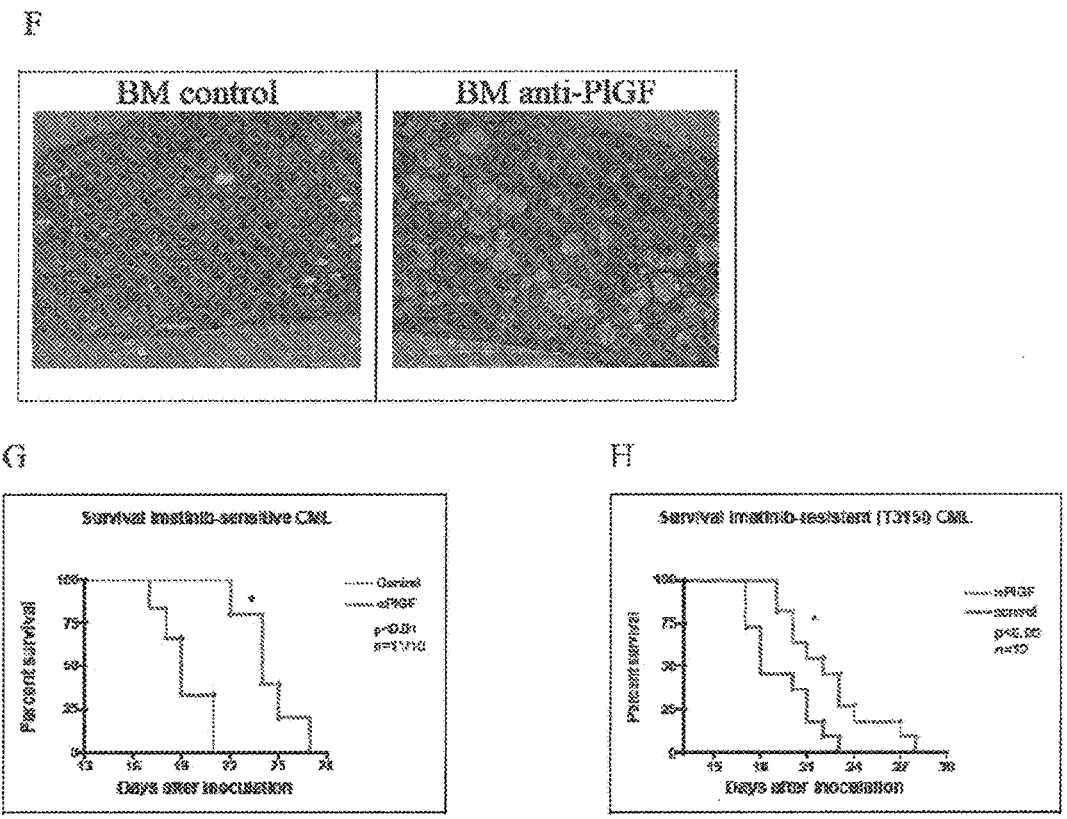

Genetic Deficiency of the Host Stroma, But Not of the Leukemia Cells Prolongs Survival of Leukemic Mice To determine the role of PIGF in BCR/ABL+ leukemia in vivo, we induced leukemia in mice genetically deficient for PIGF (PIGF$^{-/-}$) and in wt mice (WT) and compared the survival between both groups. We found that mice lacking PIGF lived significantly longer than WT mice, indicating that PIGF plays an important role in the pathogenesis of leukemia in vivo. (N=14/15 ; P=0.003; FIG. 5A).

In an attempt to proof our hypothesis that PIGF represents a stroma-derived factor in BCR/ABL+ leukemia, we performed cross-over studies by transplanting transduced bone marrow cells from WT mice and PIGF KO mice into WT hosts and compared survival between the different groups (WT→WT, KO→WT and WT→KO). We found that absence of PIGF in the leukemia cells did not prolong the survival of mice, but that PIGF deficiency of the host stroma induced a significant survival advantage in leukemic mice, which is in a comparable range as in the fully PIGF deficient system (see above). Thus, stromal derived PIGF critically promotes progression of BCR/ABL+ leukemia in vivo (FIG. 5B).

Example 6

Treatment of Leukemic Mice with Anti-PIGF Significantly Prolongs Their Survival

In order to investigate the therapeutic potential of PIGF inhibition in murine Ph+ leukemia, mice bearing leukemia induced by intravenous injection of BCR-ABL+ BaF3 cells were treated with αPIGF, and a significant prolongation of median survival by 18 days was found (N=9; P=0.015), compared to control antibodies (FIG. 5C). These results prompted us to establish murine models of imatinib-sensitive and imatinib-resistant (T315I mutant) CML, induced by transplantation of BCR-ABL transduced BM, clinically mimicking the human disease condition in blast crisis characterized by splenomegalia and excessive proliferation of myeloid leukemia cells leading to death of diseased mice one week after elevated leukocytes can be first detected in the peripheral blood. Thereafter, the effect of αPIGF on the leukemic burden, bone marrow histology and survival of mice was investigated. Reduced leukemic burden was observed (data not shown) and FACS analysis of GFP$^+$ cells at early stage (d15) and end-stage (d28) leukemia revealed specific reduction of BCR-ABL$^+$ cells in BM and PB (N=7; P<0.05) (FIGS. 5D, E and not shown). Furthermore, bone marrow histologies at end-stage indicate a substantial inhibition of disease progression induced by treatment with αPIGF (FIG. 5F). Thereafter, we investigated the effect of αPIGF on survival of mice. These experiments indicate significant prolongation of survival upon treatment with αPIGF when compared to control antibodies in mice bearing both Imatinib-sensitive and -resistant leukemia (FIGS. 5G, H). Thus, αPIGF inhibits progression of murine blast crisis leukemia independent of BCR/ABL mutational status.

Example 7

Figure 6:
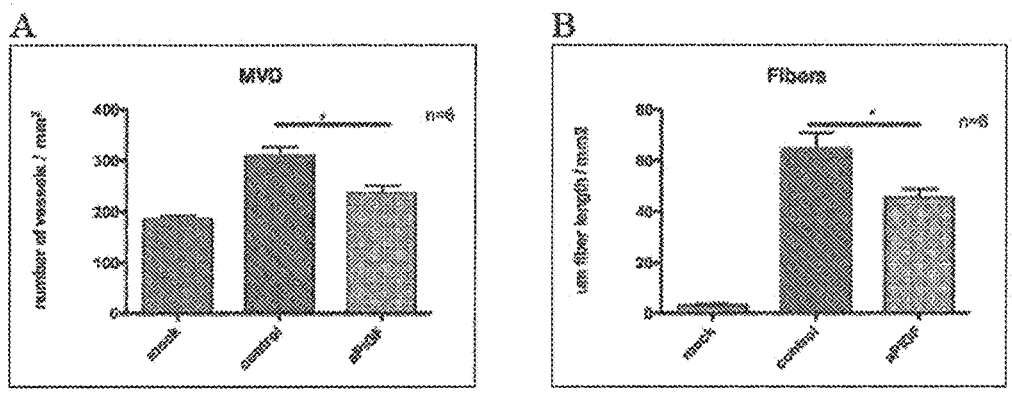
FIG. 6 shows the inhibition of bone marrow hypervascularization and fibrosis upon anti-PlGF treatment (see Example 7). A, C: bone marrow vascular density (MVD) in mock-transplanted, control antibody-treated and anti-PlGF treated mice with end-stage leukemia; B, D: length of reticulin+ fibers and bone marrow fibrosis in mock-transplanted, control antibody-treated and anti-PlGF treated mice with end-stage leukemia.
Figure 6:
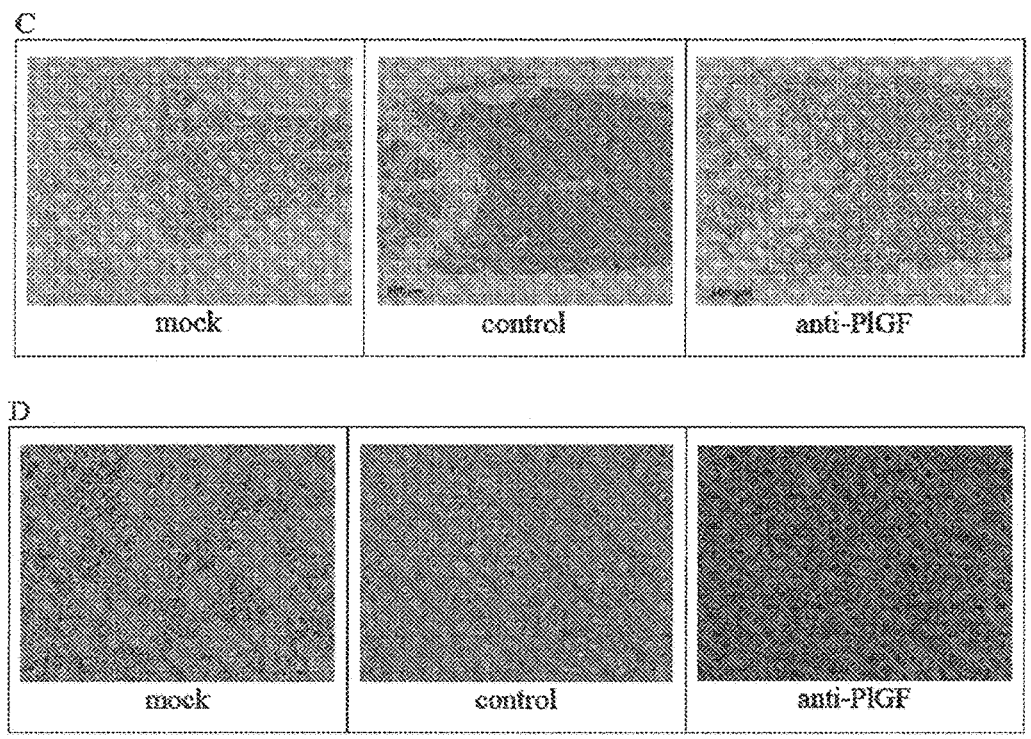

Treatment of Leukemic Mice with Anti-PIGF Inhibits Bone Marrow Hyypervascularization and Fibrosis Neoangiogenesis of the bone marrow represents an important pathogenic factor in leukemia. PIGF is a potent pro-angiogenic cytokine and was already shown to promote tumor angiogenesis. Therefore, the effect of PIGF inhibition on bone marrow vascularization was analyzed by morphometric analysis of CD31 stainings in mock-transplanted, control antibody-treated and αPIGF-treated mice with end-stage leukemia. These experiments indicated a profound hypervascularization of the bone marrow in leukemic mice compared to mock-transplanted controls (FIGS. 6 A, C). This hypervascularization is significantly reduced after treatment with αPIGF (FIGS. 6A, C).

Bone marrow fibrosis is a well known adverse factor in CML and is associated with resistance to Imatinib. Based on our observations that PIGF stimulates proliferation of BMDSCs (see above), we investigated whether treatment of leukemic mice with αPIGF could modify bone marrow fibrosis. Upon morphometric analysis of the average length of reticulin$^+$ fibers in the bone marrow we found a significant reduction of bone marrow fibrosis induced by inhibition of PIGF (FIGS. 6B, D). Hence, αPIGF reduces both hypervascularization and fibrosis of the bone marrow in leukemic mice.

Interestingly, initial experiments have shown that imatinib and anti-PIGF have an additive inhibitory effect on BCR/ABL+ leukemia in vivo.

Example 8

PIGF is Upregulated in Human CML

Figure 7:
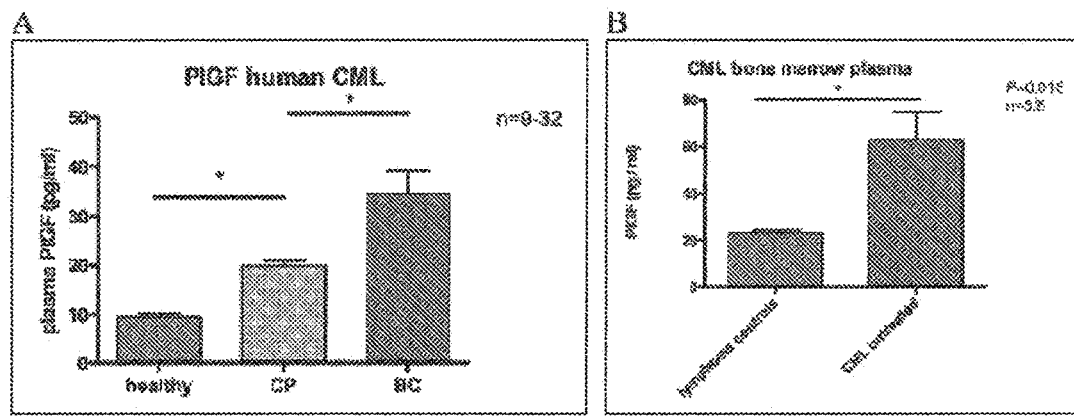
In FIG. 7, data on PlGF expression in human CML are shown (A-D, Example 8) as well as data correlating PlGF expression and imatinib treatment in mice (E) and humans (F, Example 9). A: plasma PlGF levels in different stages of CML (healthy controls, chronic phase and blast crisis), * indicates p<0.0001; B: bone marrow plasma PlGF levels in CML patients; C: correlation between PlGF levels and BCR/ABL transcript numbers in human CML; D: QRT-PCR of PlGF expression in healthy controls, leukemia cells and stromal cells of CML patients; E: bone marrow PlGF levels of untreated leukemic mice and healthy and leukemic mice treated with imatinib; F: PlGF levels in healthy human subjects and patients with different response levels to imatinib (IM). For details, see Example 9.
Figure 7:
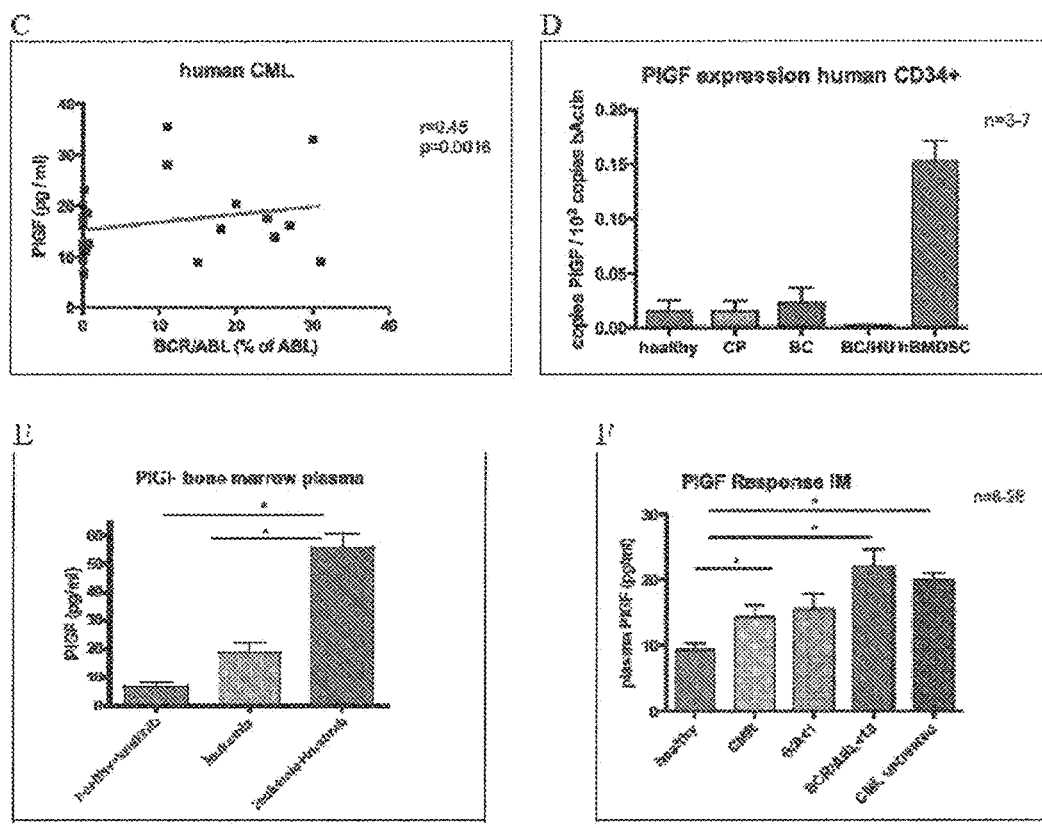

To investigate the relevance of PIGF as novel target molecule in human CML, we determined PIGF plasma levels in healthy controls (n=10), untreated patients in Chronic Phase (CP) upon primary diagnosis (n=32) and patients with blast crisis (BC, terminal phase of the disease) under treatment with different tyrosine kinase inhibitors (TKIs) (n=9). These analyses revealed 2.1-fold upregulation of PIGF in newly diagnosed patients in CP (p<0.0001) and 3.7-fold increase of PIGF levels in patients with BC (p<0.0001) compared to healthy controls (FIG. 7A). Subsequently, we determined PIGF levels in the bone marrow plasma (BMP) of patients with newly diagnosed CML (n=7) and in control patients diagnosed with lymphoma without invasion of the bone marrow (n=5; FIG. 7B). These analyses revealed an upregulation of PlGF also in BMP of CML patients compared to controls.

We then investigated a potential relation between PB PlGF protein and BCR-ABL$_1$ transcript numbers as determined by QRT-PCR in a single centre (n=43 CP, n=2 Accelerated Phase; treatment with different TKIs, imatinib+interferon, or homoharringtonine). We found a significant correlation between PlGF levels and BCR-ABL$_1$ transcript numbers (r=0.45; p=0.0016), indicating that PlGF represents a disease specific target in human CML (FIG. 7C). Subsequently, we isolated CD34$^+$ cells from healthy donors and from CML patients in CP and BC and determined PlGF expression by QRT-PCR. These analyses revealed that PlGF expression is equally low in leukemia cells as in healthy CD34$^+$ cells (FIG. 7D). Thus, elevated circulating PlGF is most likely not secreted by leukemia cells, but by stromal cells. To investigate this hypothesis, we isolated adherent BM stromal cells from patients with newly diagnosed CML and compared PlGF expression levels to those in CD34$^+$ leukemia cells. We found that stromal cells express >7-fold more PlGF than leukemia cells (FIG. 7D; p=0.003), which corroborates our preclinical data and extends the concept that PlGF is primarily produced by stromal cells in CML patients.

Example 9

PlGF Levels in CML Patients Under Imatinib Remain Elevated

It still remains unclear, why leukemia cells persist in patients treated with imatinib, which cause rapid relapse of most patients after withdrawal of the drug. The host stroma potentially plays an important role, independent of the BCR/ABL$^+$ leukemia cells. To elucidate, if imatinib can induce PlGF secretion by BMDSCs, we incubated stromal cells with increasing concentrations of imatinib. These experiments revealed dose-dependent induction of PlGF in murine BMDSCs indicating a potential role of stroma-derived PlGF in mediating resistance to imatinib. In order to elucidate whether this induction of PlGF in BMDSCs also occurs in vivo, we treated mice bearing CML induced by transplantation of BCR/ABL transduced bone marrow with imatinib and compared PlGF levels in their bone marrow with untreated leukemic mice and healthy mice. These experiments revealed upregulation of PlGF in the bone marrow of leukemic mice treated with imatinib compared to untreated mice, even though bone marrow infiltration of imatinib treated mice with leukemia cells was significantly lower (FIG. 7E) These results indicate potentiation of leukemia-induced PlGF expression in the bone marrow by imatinib, which might promote leukemia cell survival and proliferation in presence of imatinib.

These findings prompted us to determine PlGF levels in the PB of patients treated with Imatinib reaching different response levels (complete molecular remission CMR; BCR/ABL/ABL ratio <1; BCR/ABL/ABL ratio <10) and to compare them to healthy individuals and untreated, primarily diagnosed CML patients. Interestingly, PlGF levels were significantly higher in patients with CMR than in healthy subjects, and in patients with a low BCR/ABL/ABL ratio <1, PlGF was elevated to similar levels as in untreated, newly diagnosed CML patients (FIG. 7F). These data indicate that PlGF remains elevated despite reduction of leukemic burden by several orders of magnitude and might contribute to persistence of disease under treatment with Imatinib.

In conclusion, our data indicate that PlGF represents a stromal derived factor promoting the progression of Ph+ leukemia, independent of BCR/ABL mutational status, and represents a novel target produced by the leukemic stroma, useful adjunct to BCR/ABL kinase inhibitors or in TKI refractory leukemia.

Discussion

Introduction of Imatinib and second-generation BCR-ABL inhibitors has revolutionized treatment of patients with Philadelphia chromosome positive (Ph+) leukemias, but leukemia cells persist even in successfully treated patients, and some patients develop resistance and ultimately relapse. The reasons for these drawbacks are not entirely resolved, but it was postulated by us that the host stroma potentially plays an important role independent of BCR-ABL. Placental Growth Factor (PlGF), a homologue of VEGF, was already proven to be abundantly secreted by stromal cells in solid tumors. Therefore, it was decided worthwhile to study the role of PlGF in Ph+ lymphoid and myeloid leukemias, and to address the therapeutic potential of αPlGF, a monoclonal antibody against PlGF, which we recently reported to have a broad anti-tumoral potential in a variety of pre-clinical models of solid tumors (Fischer et al., Cell, 2007).

First, expression of PlGF by 5 different human and murine Ph+ leukemia cell lines (Bv-173, BaF3, 32D, K562, KCL22) was studied in vitro and none of these cell lines was found to secrete PlGF protein, although they expressed its target receptor VEGFR-1. In contrast, primary murine adherent bone marrow stromal cells (BMDSC) expressed abundant amounts of PlGF protein (up to $10^5$ pg/ml/$10^5$ cells), indicating a potential stroma-related function of PlGF.

Second, it was analyzed whether PlGF could induce proliferation and thereby dose-dependent induction of proliferation by recombinant PlGF was revealed in all analyzed leukemia cell lines. This effect of PlGF was nearly completely abrogated by both αPlGF and an extracellular anti-VEGFR-1 antibody, thus indicating that the pro-proliferative effect of PlGF is mediated primarily by VEGFR-1.

Third, potential paracrine interactions between BMDSCs and leukemia cells were studied by performing co-culture experiments. Remarkably, co-culture of BMDSC with leukemia cells significantly induced proliferation of leukemia cells. It was hypothesized that this induction of proliferation might be mediated by PlGF and indeed, nearly complete abrogation of this pro-proliferative effect upon addition of αPlGF to the co-cultures was found. Furthermore, BDMSCs significantly upregulated PlGF secretion (2.1 fold; N=3; P=0.005) when cultured in presence of leukemia cells, indicating substantial paracrine interactions between both cell types. These results allowed us to conclude, that stromal derived PlGF might represent a novel target in Ph+ leukemias.

To test this hypothesis in vivo, 3 different murine models of Ph+ myeloid and lymphoid leukemia were established. Subsequently, PlGF protein as present in blood and bone marrow of diseased mice in comparison to healthy mice was analyzed. No PlGF protein was found in the peripheral blood of healthy mice and low amounts of PlGF protein in their bone marrow. In contrast, leukemic mice showed PlGF protein (76.5±18.4 pg/ml plasma; N=7) in their circulation at levels comparable to mice bearing solid tumors, and, interestingly more than 8.9 fold (N=7; P<0.0001) elevated PlGF levels in their bone marrow, compared to healthy mice, again indicating that PlGF represents a stroma derived, novel pathogenetic factor in Ph+ leukemia.

In order to investigate the therapeutic potential of αPlGF in murine Ph+ leukemias, subsequently mice bearing leukemia induced by injection of BCR/ABL+ BaF3 cells were treated with αPlGF compared to control antibodies, and found a significant prolongation of median survival by 18 days (N=9; P=0.015) induced by αPlGF. Encouraged by these positive results, models of Imatinib-sensitive and Imatinib-resistant (T315I mutant) CML were established by transducing primary bone marrow cells and subsequent transplantation into lethally irradiated recipient mice, which were treated with αPlGF and control antibodies. Interestingly, also in these aggressive models, we found a significant prolongation of survival of diseased mice induced by blockade of PlGF (median survival prolongation in wt BCR-ABL induced leukemia 5 days; N=11; P=0.002; in T315I mutant 4 days; N=12; P=0.039). Bone marrow histology and phenotypic analysis by FACS revealed decreased infiltration of spleen and bone marrow with leukemia cells (reduction in the bone marrow by 38% and in the spleen by 24%).

We here unravel that leukemia cells instruct non-hematopoietic bone-marrow derived stromal cells (BMDSCs) to upregulate placental growth factor (PlGF), which critically drives progression of BCR-ABL1+ leukemia in pre-clinical mouse models. Importantly, these findings were confirmed in human samples of CML, as PlGF is also upregulated in blood and bone marrow of CML patients. Inhibition of this novel target molecule by a monoclonal antibody against PlGF, αPlGF, enhances survival of mice bearing Imatinib-sensitive and -resistant (T315I-mutated) leukemia. Anti-PlGF exhibits therapeutic efficacy by blocking proliferation of leukemia cells and by normalizing the abnormal leukemic bone marrow microenvironment by reducing hypervascularization and fibrosis. Interestingly, Imatinib can upregulate PlGF in BMDSCs and PlGF levels remain high in CML patients treated with Imatinib, indicating that PlGF might contribute to persistence of leukemia cells. This further supports the fact that PlGF inhibition can be used in combination with such therapies, giving additional benefit. In summary inhibition of PlGF may serve as a new candidate to be targeted in combination therapies or in TKI refractory CML.

In conclusion, these data indicate that PlGF represents a stromal derived factor promoting the progression of Ph+ leukemia, independent of BCR-ABL mutational status, and might represent a novel target produced by the leukemic stroma, potentially useful adjunct to BCR-ABL kinase inhibitors.

REFERENCES

Aiello L P, Pierce E A, Foley E D, Takagi H, Chen H, Riddle L, Ferrara N, King G L, Smith L E. Suppression of retinal neovascularization in vivo by inhibition of vascular endothelial growth factor (VEGF) using soluble VEGF-receptor chimeric proteins. Proc Natl Acad Sci USA. 1995; 92(23):10457-61.

Altman S. RNase P in research and therapy. Biotechnology (N Y). 1995; 13(4):327-9.

Alvarado Y, Apostolidou E, Swords R, Giles F J. Emerging therapeutic options for Philadelphia-positive acute lymphocytic leukemia. Expert Opin Emerg Drugs. 2007; 12(1): 165-79.

Berard M, Sordello S, Ortega N, Carrier J L, Peyri N, Wassef M, Bertrand N, Enjolras O, Drouet L, Plouet J. Vascular endothelial growth factor confers a growth advantage in vitro and in vivo to stromal cells cultured from neonatal hemangiomas. Am J Pathol. 1997; 150(4):1315-26.

Bridonneau P, Bunch S, Tengler R, Hill K, Carter J, Pieken W, Tinnermeier D, Lehrman R, Drolet D W. Purification of a highly modified RNA-aptamer. Effect of complete denaturation during chromatography on product recovery and specific activity. J Chromatogr B Biomed Sci Appl. 1999 Apr 16;726(1-2):237-47.

Burchert A. Roots of imatinib resistance: a question of self-renewal? Drug Resist Updat. 2007; 10(4-5):152-61.

Corbin A S, La Rosée P, Stoffregen E P, Druker B J, Deininger M W. Several Bcr-Abl kinase domain mutants associated with imatinib mesylate resistance remain sensitive to imatinib. Blood. 2003; 101(11):4611-4.

Cristiano R J, Smith L C, Kay M A, Brinkley B R, Woo S L. Hepatic gene therapy: efficient gene delivery and expression in primary hepatocytes utilizing a conjugated adenovirus-DNA complex. Proc Natl Acad Sci USA. 1993; 90(24):11548-52.

Culver K W, Vickers T M, Lamsam J L, Walling H W, Seregina T. Gene therapy for solid tumors. Br Med Bull. 1995; 51(1):192-204.

Davis. Kinetic Characterization of Thrombin-Aptamer Interactions. Pharmacia Biosensor Application Note 1994; 305.

Ellington A D, Szostak J W. In vitro selection of RNA molecules that bind specific ligands. Nature. 1990; 346 (6287):818-22.

Fader S, Talpaz M, Estrov Z, Kantarjian H M. Chronic myelogenous leukemia: biology and therapy. Ann Intern Med. 1999; 131(3):207-19.

Fernandez J M, Chu S, Oberhauser A F. RNA structure. Pulling on hair (pins). Science. 2001; 292(5517):653-4.

Fire A, Xu S, Montgomery M K, Kostas S A, Driver S E, Mello C C. Potent and specific genetic interference by double-stranded RNA in Caenorhabditis elegans. Nature. 1998; 391(6669):806-11.

Fischer C, Jonckx B, Mazzone M, Zacchigna S, Loges S, Pattarini L, Chorianopoulos E, Liesenborghs L, Koch M, De Mol M, Autiero M, Wyns S, Plaisance S, Moons L, van Rooijen N, Giacca M, Stassen J M, Dewerchin M, Collen D, Carmeliet P. Anti-PlGF inhibits growth of VEGF(R)-inhibitor-resistant tumors without affecting healthy vessels. Cell. 2007; 131(3):463-75.

Fragoso R, Pereira T, Wu Y, Zhu Z, Cabecadas J, Dias S. VEGFR-1 (FLT-1) activation modulates acute lymphoblastic leukemia localization and survival within the bone marrow, determining the onset of extramedullary disease. Blood. 2006; 107(4):1608-16.

Gold L, Polisky B, Uhlenbeck O, Yarus M. Diversity of oligonucleotide functions. Annu Rev Biochem. 1995; 64:763-97.

Hehlmann R, Hochhaus A, Baccarani M; European LeukemiaNet. Chronic myeloid leukaemia. Lancet. 2007; 370 (9584):342-50.

Ikai T, Miwa H, Shikami M, Hiramatsu A, Tajima E, Yamamoto H, Imai N, Hattori A, Nishii K, Miura K, Satoh A, Itoh M, Imamura A, Mihara H, Katoh Y, Nitta M. Placenta growth factor stimulates the growth of Philadelphia chromosome positive acute lymphoblastic leukemia cells by both autocrine and paracrine pathways. Eur J Haematol. 2005; 75(4):273-9.

Jenke A C, Stehle I M, Herrmann F, Eisenberger T, Baiker A, Bode J, Fackelmayer F O, Lipps H J. Nuclear scaffold/matrix attached region modules linked to a transcription unit are sufficient for replication and maintenance of a mammalian episome. Proc Natl Acad Sci USA. 2004; 101(31): 11322-7.

Jones P T, Dear P H, Foote J, Neuberger M S, Winter G. Replacing the complementarity-determining regions in a human antibody with those from a mouse. Nature. 1986; 321(6069):522-5.

Kendall R L, Wang G, Thomas K A. Identification of a natural soluble form of the vascular endothelial growth factor receptor, FLT-1, and its heterodimerization with KDR. Biochem Biophys Res Commun. 1996; 226(2):324-8.

Korth C, Stierli B, Streit P, Moser M, Schaller O, Fischer R, Schulz-Schaeffer W, Kretzschmar H, Raeber A, Braun U, Ehrensperger F, Hornemann S, Glockshuber R, Riek R, Billeter M, Wüthrich K, Oesch B. Prion (PrPSc)-specific epitope defined by a monoclonal antibody. Nature. 1997; 390(6655):74-7.

Kujawski L, Talpaz M. Strategies for overcoming imatinib resistance in chronic myeloid leukemia. Leuk Lymphoma. 2007; 48(12):2310-22.

Lam K S, Salmon S E, Hersh E M, Hruby V J, Kazmierski W M, Knapp R J. A new type of synthetic peptide library for identifying ligand-binding activity. Nature. 1991; 354 (6348):82-4.

Ledley F D. Nonviral gene therapy: the promise of genes as pharmaceutical products. Hum Gene Ther. 1995; 6(9): 1129-44.

Li S, Li D. Stem cell and kinase activity-independent pathway in resistance of leukaemia to BCR-ABL kinase inhibitors. J Cell Mol Med. 2007; 11(6):1251-62.

Manzini S, Vargiolu A, Stehle I M, Bacci M L, Cerrito M G, Giovannoni R, Zannoni A, Bianco M R, Forni M, Donini P, Papa M, Lipps H J, Lavitrano M. Genetically modified pigs produced with a nonviral episomal vector. Proc Natl Acad Sci USA. 2006; 103(47):17672-7.

Marchand G S, Noiseux N, Tanguay J F, Sirois M G. Blockade of in vivo VEGF-mediated angiogenesis by antisense gene therapy: role of Flk-1 and Flt-1 receptors. Am J Physiol Heart Circ Physiol. 2002; 282(1):H194-204.

Matteucci M D, Wagner R W. In pursuit of antisense. Nature. 1996; 384(6604 Suppl):20-2.

Melo J V. The molecular biology of chronic myeloid leukaemia. Leukemia. 1996; 10(5):751-6.

Miller A D. Retrovirus packaging cells. Hum Gene Ther. 1990; 1(1):5-14.

Naldini L, Blömer U, Gallay P, Ory D, Mulligan R, Gage F H, Verma I M, Trono D. In vivo gene delivery and stable transduction of nondividing cells by a lentiviral vector. Science. 1996; 272(5259):263-7.

Pavco P A, Bouhana K S, Gallegos A M, Agrawal A, Blanchard K S, Grimm S L, Jensen K L, Andrews L E, Wincott F E, Pitot P A, Tressler R J, Cushman C, Reynolds M A, Parry T J. Antitumor and antimetastatic activity of ribozymes targeting the messenger RNA of vascular endothelial growth factor receptors. Clin Cancer Res. 2000; 6(5):2094-103.

Piccaluga P P, Martinelli G, Rondoni M, Visani G, Baccarani M. Advances and potential treatment for Philadelphia chromosome-positive adult acute lymphoid leukaemia. Expert Opin Biol Ther. 2006; 6(10):1011-22.

Radich J P. Philadelphia chromosome-positive acute lymphocytic leukemia. Hematol Oncol Clin North Am. 2001; 15(1):21-36.

Riechmann L, Clark M, Waldmann H, Winter G. Reshaping human antibodies for therapy. Nature. 1988; 332(6162): 323-7.

Ruckman J, Green L S, Beeson J, Waugh S, Gillette W L, Henninger D D, Claesson-Welsh L, Janjić N. 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J Biol Chem. 1998; 273(32):20556-67.

Shah N P, Sawyers C L. Mechanisms of resistance to STI571 in Philadelphia chromosome-associated leukemias. Oncogene. 2003; 22(47):7389-95.

Shibuya M. Structure and function of VEGF/VEGF-receptor system involved in angiogenesis. Cell Struct Funct. 2001; 26(1):25-35.

Silver R T. Chronic myeloid leukemia. Hematol Oncol Clin North Am. 2003; 17:1159-1173.

Swords R, Alvarado Y, Giles F. Novel Abl kinase inhibitors in chronic myeloid leukemia in blastic phase and Philadelphia chromosome-positive acute lymphoblastic leukemia. Clin Lymphoma Myeloma. 2007; 7 Suppl 3:S113-9.

Trapnell B C. Adenoviral vectors for gene transfer. Adv. Drug Del. Rev. 1993; 12: 185-199.

Tuerk C, Gold L. Systematic evolution of ligands by exponential enrichment: RNA ligands to bacteriophage T4 DNA polymerase. Science. 1990; 249(4968):505-10.

Weng D E, Usman N. Angiozyme: a novel angiogenesis inhibitor. Curr Oncol Rep. 2001; 3(2):141-6.

Yamada T, Iwasaki Y, Tada H, Iwabuki H, Chuah M K, VandenDriessche T, Fukuda H, Kondo A, Ueda M, Seno M, Tanizawa K, Kuroda S. Nanoparticles for the delivery of genes and drugs to human hepatocytes. Nat Biotechnol. 2003; 21(8):885-90.

Yanada M, Naoe T. Imatinib combined chemotherapy for Philadelphia chromosome-positive acute lymphoblastic leukemia: major challenges in current practice. Leuk Lymphoma. 2006 Sep; 47(9):1747-53.

Yonekura H, Sakurai S, Liu X, Migita H, Wang H, Yamagishi S, Nomura M, Abedin M J, Unoki H, Yamamoto Y, Yamamoto H. Placenta growth factor and vascular endothelial growth factor B and C expression in microvascular endothelial cells and pericytes. Implication in autocrine and paracrine regulation of angiogenesis. J Biol Chem. 1999; 274(49):35172-8.

What is claimed is:

1. A method of treating Philadelphia chromosome positive chronic myelogenous leukemia (Ph+CML) in a subject in need thereof, comprising administering a therapeutically effective amount of a monoclonal antibody or a fragment thereof to treat Ph+CML in said subject; wherein said monoclonal antibody or fragment thereof comprises the complementarity determining regions (CDRs) SEQ ID NO: 1, SEQ ID NO: 2, SEQ ID NO:3, SEQ ID NO: 4, SEQ ID NO: 5, and SEQ ID NO: 6.

2. The method according to claim 1, wherein the subject is treated with a BCR-ABL inhibitor.

3. The method according to claim 1, wherein the monoclonal antibody or fragment thereof specifically binding to PlGF is a humanised monoclonal antibody or a fragment thereof specifically binding to PlGF.

4. The method according to claim 1, wherein said subject has been previously treated with a BCR-ABL inhibitor and developed insensitivity of malignant cells to the BCR-ABL inhibitor due to resistance or partial resistance to the BCR-ABL inhibitor.

5. The method according to claim 1, wherein said BCR-ABL inhibitor is imatinib.

6. The method according to claim 1, wherein the subject has been previously treated with a BCR-ABL inhibitor, and either (a) developed insensitivity of malignant cells to the BCR-ABL inhibitor, or (b) the BCR-ABL inhibitor was not tolerated by the patient.

7. The method according to claim 1, wherein the monoclonal antibody or fragment thereof comprises SEQ ID NO: 1 and SEQ ID NO: 8.

8. The method according to claim 7, wherein the monoclonal antibody is the 16D3 antibody as produced by the cell line deposited as LMBP 6399CB.

9. The method according to claim 1, wherein the monoclonal antibody or fragment thereof comprises a single-chain variable fragment comprising SEQ ID NO: 9.

10. The method according to claim 1, wherein the monoclonal antibody or fragment thereof comprises SEQ ID NO: 10 and SEQ ID NO: 11.

11. The method according to claim 1, wherein the monoclonal antibody or fragment thereof comprises a single-chain variable fragment comprising SEQ ID NO: 12.

* * * * *

SEQUENCE LISTING

```
<160> NUMBER OF SEQ ID NOS: 12

<210> SEQ ID NO 1
<211> LENGTH: 8
<212> TYPE: PRT
<213> ORGANISM: Mus musculus
<220> FEATURE:
<221> NAME/KEY: misc_feature
<222> LOCATION: (1)..(8)
<223> OTHER INFORMATION: CDR1 heavy chain 16D3
```

```
<400> SEQUENCE: 1

Gly Tyr Thr Phe Thr Asp Tyr Tyr
1               5

<210> SEQ ID NO 2
<211> LENGTH: 8
<212> TYPE: PRT
<213> ORGANISM: mus musculus
<220> FEATURE:
<221> NAME/KEY: misc_feature
<222> LOCATION: (1)..(8)
<223> OTHER INFORMATION: CDR2 heavy chain 16D3

<400> SEQUENCE: 2

Ile Tyr Pro Gly Ser Gly Asn Thr
1               5

<210> SEQ ID NO 3
<211> LENGTH: 9
<212> TYPE: PRT
<213> ORGANISM: mus musculus
<220> FEATURE:
<221> NAME/KEY: misc_feature
<222> LOCATION: (1)..(9)
<223> OTHER INFORMATION: CDR3 heavy chain 16D3

<400> SEQUENCE: 3

Val Arg Asp Ser Pro Phe Phe Asp Tyr
1               5

<210> SEQ ID NO 4
<211> LENGTH: 12
<212> TYPE: PRT
<213> ORGANISM: mus musculus
<220> FEATURE:
<221> NAME/KEY: misc_feature
<222> LOCATION: (1)..(12)
<223> OTHER INFORMATION: CDR1 light chain 16D3

<400> SEQUENCE: 4

Gln Ser Leu Leu Asn Ser Gly Met Arg Lys Ser Phe
1               5                   10

<210> SEQ ID NO 5
<211> LENGTH: 4
<212> TYPE: PRT
<213> ORGANISM: mus musculus
<220> FEATURE:
<221> NAME/KEY: miisc
<222> LOCATION: (1)..(3)
<223> OTHER INFORMATION: CDR2 light chain 16D3, Xaa= flanking amino
      acid not part of CDR
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Trp Ala Ser Xaa
1

<210> SEQ ID NO 6
<211> LENGTH: 8
<212> TYPE: PRT
<213> ORGANISM: mus musculus
<220> FEATURE:
<221> NAME/KEY: misc_feature
<222> LOCATION: (1)..(8)
<223> OTHER INFORMATION: CDR3 light chain 16D3
```

<400> SEQUENCE: 6

Lys Gln Ser Tyr His Leu Phe Thr
1               5

<210> SEQ ID NO 7
<211> LENGTH: 348
<212> TYPE: PRT
<213> ORGANISM: mus musculus

<400> SEQUENCE: 7

Cys Ala Gly Ala Thr Cys Cys Ala Gly Cys Thr Gly Cys Ala Gly Cys
1               5                   10                  15

Ala Gly Thr Cys Thr Gly Gly Ala Cys Cys Thr Gly Ala Gly Cys Thr
                20                  25                  30

Gly Gly Thr Gly Ala Ala Gly Cys Cys Thr Gly Gly Gly Gly Cys Thr
            35                  40                  45

Thr Cys Ala Gly Thr Gly Ala Ala Gly Ala Thr Ala Thr Cys Cys Thr
        50                  55                  60

Gly Cys Ala Ala Gly Gly Cys Cys Thr Cys Thr Gly Gly Cys Thr Ala
65                  70                  75                  80

Cys Ala Cys Cys Thr Thr Cys Ala Cys Thr Gly Ala Cys Thr Ala Cys
                85                  90                  95

Thr Ala Thr Ala Thr Ala Ala Ala Cys Thr Gly Gly Thr Gly Ala
                100                 105                 110

Ala Gly Thr Thr Gly Ala Ala Gly Cys Cys Thr Gly Gly Ala Cys Ala
            115                 120                 125

Gly Gly Gly Ala Cys Thr Thr Gly Ala Gly Thr Gly Gly Ala Thr Thr
        130                 135                 140

Gly Gly Ala Thr Gly Gly Ala Thr Thr Thr Ala Thr Cys Cys Thr Gly
145                 150                 155                 160

Gly Ala Ala Gly Cys Gly Gly Thr Ala Ala Thr Ala Cys Thr Ala Ala
                165                 170                 175

Gly Thr Ala Cys Ala Ala Thr Gly Ala Gly Ala Ala Gly Thr Thr Cys
                180                 185                 190

Ala Ala Gly Gly Gly Cys Ala Ala Gly Gly Cys Cys Ala Cys Ala Thr
            195                 200                 205

Thr Gly Ala Cys Thr Ala Thr Ala Gly Ala Cys Ala Cys Ala Thr Cys
        210                 215                 220

Cys Thr Cys Cys Ala Gly Cys Ala Cys Ala Gly Cys Cys Thr Ala Cys
225                 230                 235                 240

Ala Thr Gly Cys Ala Gly Cys Thr Cys Ala Gly Cys Ala Gly Cys Cys
                245                 250                 255

Thr Gly Ala Cys Ala Thr Cys Thr Gly Ala Gly Gly Ala Cys Ala Cys
                260                 265                 270

Thr Gly Cys Thr Gly Thr Cys Thr Ala Thr Thr Cys Thr Gly Thr
            275                 280                 285

Gly Thr Ala Ala Gly Ala Gly Ala Cys Ala Gly Cys Cys Cys Thr Thr
        290                 295                 300

Thr Cys Thr Thr Thr Gly Ala Cys Thr Ala Cys Thr Gly Gly Gly Gly
305                 310                 315                 320

Cys Cys Ala Ala Gly Gly Cys Ala Cys Cys Ala Cys Thr Cys Thr Cys
                325                 330                 335

Ala Cys Ala Gly Thr Cys Thr Cys Cys Thr Cys Ala
                340                 345

<210> SEQ ID NO 8
<211> LENGTH: 336
<212> TYPE: PRT
<213> ORGANISM: mus musculus

<400> SEQUENCE: 8

Gly Ala Cys Ala Thr Gly Thr Gly Cys Thr Gly Cys Ala Cys
1               5                   10                  15

Ala Gly Thr Cys Thr Cys Cys Ala Cys Cys Thr Cys Cys Cys Thr
                20                  25                  30

Gly Gly Cys Thr Gly Thr Gly Thr Cys Ala Gly Cys Ala Gly Gly Ala
            35                  40                  45

Gly Ala Gly Ala Ala Gly Gly Thr Cys Ala Cys Thr Ala Thr Gly Cys
        50                  55                  60

Gly Cys Thr Gly Cys Ala Ala Ala Thr Cys Cys Ala Gly Thr Cys Ala
65                  70                  75                  80

Gly Ala Gly Thr Cys Thr Gly Cys Thr Cys Ala Ala Cys Ala Gly Thr
                85                  90                  95

Gly Gly Ala Ala Thr Gly Cys Gly Ala Ala Gly Ala Gly Thr Thr
            100                 105                 110

Thr Cys Thr Thr Gly Gly Cys Thr Thr Gly Gly Thr Ala Cys Cys Ala
        115                 120                 125

Gly Cys Ala Gly Ala Ala Cys Cys Ala Gly Gly Cys Ala Gly
        130                 135                 140

Thr Cys Thr Cys Cys Thr Ala Ala Gly Cys Thr Gly Cys Thr Gly Ala
145                 150                 155                 160

Thr Cys Thr Ala Cys Thr Gly Gly Gly Cys Ala Thr Cys Cys Ala Cys
                165                 170                 175

Thr Ala Gly Gly Gly Ala Ala Thr Cys Thr Gly Gly Gly Gly Thr Cys
            180                 185                 190

Cys Cys Thr Gly Ala Thr Cys Gly Cys Thr Thr Cys Ala Cys Ala Gly
        195                 200                 205

Gly Cys Ala Gly Thr Gly Gly Ala Thr Cys Thr Gly Gly Gly Ala Cys
        210                 215                 220

Ala Gly Ala Thr Thr Thr Cys Ala Cys Thr Cys Thr Ala Cys Cys
225                 230                 235                 240

Ala Thr Cys Ala Gly Cys Ala Gly Thr Gly Thr Cys Ala Gly Gly
                245                 250                 255

Cys Thr Gly Ala Ala Gly Ala Cys Cys Thr Gly Gly Cys Ala Gly Thr
            260                 265                 270

Thr Thr Ala Thr Thr Ala Cys Thr Gly Cys Ala Ala Gly Cys Ala Ala
        275                 280                 285

Thr Cys Thr Thr Ala Thr Cys Ala Thr Ala Thr Cys Ala
        290                 295                 300

Cys Gly Thr Thr Cys Gly Gly Cys Thr Cys Gly Gly Gly Gly Ala Cys
305                 310                 315                 320

Ala Ala Ala Gly Thr Thr Gly Gly Ala Ala Thr Ala Ala Ala
                325                 330                 335

<210> SEQ ID NO 9
<211> LENGTH: 262
<212> TYPE: PRT
<213> ORGANISM: Artificial sequence
<220> FEATURE:
<223> OTHER INFORMATION: Synthetic construct

<400> SEQUENCE: 9

```
Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Leu Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ile Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Thr Leu
            100                 105                 110

Thr Val Ser Ser Gly Gly Gly Gly Ser Gly Gly Gly Gly Ser Gly Gly
        115                 120                 125

Gly Gly Ser Asp Ile Val Leu Ser Gln Ser Pro Ser Ser Leu Ala Val
    130                 135                 140

Ser Ala Gly Glu Lys Val Thr Met Arg Cys Lys Ser Ser Gln Ser Leu
145                 150                 155                 160

Leu Asn Ser Gly Met Arg Lys Ser Phe Leu Ala Trp Tyr Gln Gln Lys
                165                 170                 175

Pro Gly Gln Ser Pro Lys Leu Leu Ile Tyr Trp Ala Ser Thr Arg Glu
            180                 185                 190

Ser Gly Val Pro Asp Arg Phe Thr Gly Ser Gly Ser Gly Thr Asp Phe
        195                 200                 205

Thr Leu Thr Ile Ser Ser Val Gln Ala Glu Asp Leu Ala Val Tyr Tyr
    210                 215                 220

Cys Lys Gln Ser Tyr His Leu Phe Thr Phe Gly Ser Gly Thr Lys Leu
225                 230                 235                 240

Glu Ile Lys Gly Ser Tyr Pro Tyr Asp Val Pro Asp Tyr Ala Gly Ser
                245                 250                 255

His His His His His His
            260
```

<210> SEQ ID NO 10
<211> LENGTH: 116
<212> TYPE: PRT
<213> ORGANISM: Artificial sequence
<220> FEATURE:
<223> OTHER INFORMATION: Synthetic construct

<400> SEQUENCE: 10

```
Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Leu Ala Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ile Asp Thr Ser Ser Ser Thr Ala Tyr
65                  70                  75                  80
```

```
Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Leu Leu
            100                 105                 110

Thr Val Ser Ser
        115

<210> SEQ ID NO 11
<211> LENGTH: 112
<212> TYPE: PRT
<213> ORGANISM: Artificial sequence
<220> FEATURE:
<223> OTHER INFORMATION: Synthetic construct

<400> SEQUENCE: 11

Asp Ile Val Leu Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Met Arg Lys Ser Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Val Ala Val Tyr Tyr Cys Lys Gln
                85                  90                  95

Ser Tyr His Leu Phe Thr Phe Gly Ser Gly Thr Lys Leu Glu Ile Lys
            100                 105                 110

<210> SEQ ID NO 12
<211> LENGTH: 262
<212> TYPE: PRT
<213> ORGANISM: Artificial sequence
<220> FEATURE:
<223> OTHER INFORMATION: Synthetic construct

<400> SEQUENCE: 12

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Leu Ala Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ile Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Leu Leu
            100                 105                 110

Thr Val Ser Ser Gly Gly Gly Gly Ser Gly Gly Gly Gly Ser Gly Gly
            115                 120                 125

Gly Gly Ser Asp Ile Val Leu Thr Gln Ser Pro Asp Ser Leu Ala Val
        130                 135                 140

Ser Leu Gly Glu Arg Val Thr Met Asn Cys Lys Ser Ser Gln Ser Leu
145                 150                 155                 160
```

```
Leu Asn Ser Gly Met Arg Lys Ser Phe Leu Ala Trp Tyr Gln Gln Lys
                165             170                 175

Pro Gly Gln Ser Pro Lys Leu Leu Ile Tyr Trp Ala Ser Thr Arg Glu
            180             185                 190

Ser Gly Val Pro Asp Arg Phe Thr Gly Ser Gly Ser Gly Thr Asp Phe
        195             200             205

Thr Leu Thr Ile Ser Ser Val Gln Ala Glu Asp Val Ala Val Tyr Tyr
        210             215             220

Cys Lys Gln Ser Tyr His Leu Phe Thr Phe Gly Ser Gly Thr Lys Leu
225             230             235                 240

Glu Ile Lys Gly Ser Tyr Pro Tyr Asp Val Pro Asp Tyr Ala Gly Ser
            245             250             255

His His His His His His
            260
```